(12) United States Patent
Patterson et al.

(10) Patent No.: US 12,090,128 B2
(45) Date of Patent: *Sep. 17, 2024

(54) DISPERSIBLE FORMULATIONS OF N-((R)-2,3-DIHYDROXYPROPOXY)-3,4-DIFLUORO-2-(2-FLUORO-4-IODO-PHENYLAMINO)-BENAZMIDE AND USES THEREOF

(71) Applicant: SpringWorks Therapeutics, Inc., Stamford, CT (US)

(72) Inventors: Kristin Patterson, Stamford, CT (US); Jiping Liu, Stamford, CT (US)

(73) Assignee: SPRINGWORKS THERAPEUTICS, INC., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/429,056

(22) Filed: Jan. 31, 2024

(65) Prior Publication Data

US 2024/0216307 A1    Jul. 4, 2024

Related U.S. Application Data

(60) Continuation of application No. 18/151,707, filed on Jan. 9, 2023, which is a division of application No. 17/177,999, filed on Feb. 17, 2021, now Pat. No. 11,571,402.

(51) Int. Cl.
| | | |
|---|---|---|
| *A61K 31/167* | (2006.01) | |
| *A61K 9/00* | (2006.01) | |
| *A61K 9/16* | (2006.01) | |
| *A61K 9/20* | (2006.01) | |

(52) U.S. Cl.
CPC .......... *A61K 31/167* (2013.01); *A61K 9/0056* (2013.01); *A61K 9/16* (2013.01); *A61K 9/2013* (2013.01); *A61K 9/2018* (2013.01); *A61K 9/2054* (2013.01); *A61K 9/2072* (2013.01)

(58) Field of Classification Search
CPC ..................................................... A61K 31/167
See application file for complete search history.

(56) References Cited

U.S. PATENT DOCUMENTS

| | | | |
|---|---|---|---|
| 6,960,614 B2 | 11/2005 | Barrett et al. | |
| 7,060,856 B2 | 6/2006 | Macikenas et al. | |
| 7,411,001 B2 | 8/2008 | Barrett et al. | |
| 11,066,358 B1 * | 7/2021 | Irdam | A61P 35/00 |
| 11,084,780 B1 * | 8/2021 | Patterson | A61K 9/4825 |
| 11,453,641 B2 * | 9/2022 | Irdam | A61K 9/20 |

(Continued)

FOREIGN PATENT DOCUMENTS

| | | |
|---|---|---|
| WO | 2002006213 A2 | 1/2002 |
| WO | 2004045617 A1 | 6/2004 |

(Continued)

OTHER PUBLICATIONS

Dombi, E., et al., "NF1 plexiform neurofibroma growth rate by volumetric MRI: relationship to age and body weight," Neurology 68(9):643-647, Lippincott Williams and Wilkins Ltd., United States (Feb. 2007).

(Continued)

*Primary Examiner* — Carlos A Azpuru
(74) *Attorney, Agent, or Firm* — Blank Rome LLP

(57) ABSTRACT

The present disclosure relates to dispersible pharmaceutical compositions comprising N—((R)-2,3-dihydroxypropoxy)-3,4-difluoro-2-(2-fluoro-4-iodo-phenylamino)-benzamide, and, optionally, a pharmaceutically acceptable carrier.

23 Claims, 4 Drawing Sheets

(56) References Cited

U.S. PATENT DOCUMENTS

| | | | |
|---|---|---|---|
| 11,571,402 B2* | 2/2023 | Patterson | A61K 9/16 |
| 11,884,610 B2* | 1/2024 | Patterson | A61K 9/2013 |
| 2022/0257543 A1 | 8/2022 | Patterson et al. | |

FOREIGN PATENT DOCUMENTS

| | | |
|---|---|---|
| WO | 2005040098 A1 | 5/2005 |
| WO | 2006061712 A1 | 6/2006 |
| WO | 2006134469 A1 | 12/2006 |
| WO | 2007042885 A2 | 4/2007 |

OTHER PUBLICATIONS

NCT00147550, "A Multicenter, Open-Label, Noncomparative Phase 1-2 Clinical And Pharmacokinetic Study Of Oral PD 0325901 In Patients With Advanced Cancer," sponsored by Pfizer, first posted Sep. 7, 2005, accessed at https://clinicaltrials.gov/ct2/show/record/NCT00147550 on Feb. 22, 2021, 3 pages.

NCT00174369, "Phase 2 Study Of The MEK InhibitorPD-0325901 In Patients With Advanced Non-Small Cell Lung Cancer," sponsored by Pfizer, first posted Sep. 15, 2005, accessed at https://clinicaltrials.gov/ct2/show/record/NCT00174369 on Feb. 22, 2021, 3 pages.

NCT01347866, "A Multi-arm Phase 1 Dose Escalation Study Of The Safety, Pharmacokinetics, And Pharmacodynamics Of The Dual Pi3k/Mtor Inhibitors Pf-04691502 And Pf-05212384 In Combination With Experimental Or Approved Anticancer Agents In Patients With Advanced Cancer," sponsored by Pfizer, first posted May 4, 2011, accessed at https://clinicaltrials.gov/ct2/show/record/NCT01347866 on Feb. 22, 2021, 6 pages.

NCT02022982, "Phase 1/11 Study of the CDK4/6 Inhibitor Palbociclib (PD-0332991) in Combination With the MEK Inhibitor PD-0325901 for Patients With KRAS Mutant Non-Small Cell Lung Cancer and Other Solid Tumors," sponsored by Dana-Farber Cancer Institute, first posted Dec. 30, 2013, accessed at https://clinicaltrials.gov/ct2/show/record/NCT02022982 onFeb. 22, 2021, 4 pages.

NCT02039336, "Phase 1/11 Study With the Combination ofDacomitinib and PD-0325901 in Metastatic KRAS Mutation Positive Non-small Cell Lung Cancer," sponsored by The Netherlands Cancer Institute, first posted Jan. 17, 2014, accessed at https://clinicaltrials.gov/ct2/show/record/NCT02039336 on Feb. 22, 2021, 3 pages.

NCT02096471, "A Phase 2 Trial of the MEK Inhibitor PD-0325901 in Adolescents and Adults With NFI-Associated Morbid Plexiform Neurofibromas," sponsored by University of Alabama at Birmingham, first posted Mar. 26, 2014, accessed at https://clinicaltrials.gov/ct2/show/NCT02096471 on Feb. 22, 2021, 6 pages.

NCT02510001, "A Sequential Phase I Study of MEKI/2 Inhibitors PD-0325901 or Binimetinib Combined With cMET Inhibitor PF-02341066 in Patients With RAS Mutant and RAS Wild Type (With Aberrant c-MET) Colorectal Cancer," sponsored by University of Oxford, first posted Jul. 28, 2015, accessed at https://clinicaltrials.gov/ct2/show/record/ NCT02510001on Feb. 22, 2021, 11 pages.

NCT03 I 70206, "Phase 1/11 Study of the CDK4/6 Inhibitor Palbociclib (PD-0332991) in Combination With the MEK Inhibitor Binimetinib (MEK162) for Patients With Advanced KRAS Mutant Non-Small Cell Lung Cancer," sponsored by Dana-Farber Cancer Institute, first posted May 30, 2017, accessed at https://clinicaltrials.gov/ct2/show/record/NCT03 I 70206 on Feb. 22, 2021, 5 pages.

NCT03905148, "A Phase Ib, Open-Label, Dose-escalation and Expansion Study to Investigate the Safety, Pharmacokinetics and Antitumor Activities of a RAF Dimer Inhibitor BGB-283 in Combination With MEK Inhibitor PD-0325901 in Patients With Advanced or Refractory Solid Tumors," sponsored by BeiGene, first posted Apr. 5, 2019, accessed at https://clinicaltrials.gov/ct2/show/record/NCT03905148 on Feb. 22, 2021, 4 pages.

NCT03962543, "A Phase 2b Trial of the MEK 1/2 Inhibitor (MEKi) PD-0325901 in Adult and Pediatric Patients With Neurofibromatosis Type 1 (NFI)-Associated Inoperable Plexiform Neurofibromas (PNs) That Are Causing Significant Morbidity," sponsored by SpringWorks Therapeutics, Inc., first posted May 24, 2019, accessed at https://clinicaltrials.gov/ct2/show/NCT03962543 on Feb. 22, 2021, 4 pages.

Nguyen, R., et al., "Growth dynamics of plexiform neurofibromas: a retrospective cohort study of 201 patients with neurofibromatosis I," Orphanet Journal of Rare Diseases 7:75, BioMed Central Ltd., United Kingdom (Oct. 2012).

Prada, C. E., et al., "Pediatric plexiform neurofibromas: impact on morbidity and mortality in neurofibromatosis type I," The Journal of Pediatrics 160(3):461-467, Mosby Inc., United States (Mar. 2012).

Rasmussen, S. A., et al., "Mortality in neurofibromatosis 1: an analysis using U.S. death certificates," American Journal of Human Genetics 68(5):1110-1118, Cell Press, United States (May 2001).

Tucker, T., et al., "Longitudinal study of neurofibromatosis 1 associated plexiform neurofibromas," American Journal of Medical Genetics 46(2):81-85, Wiley-Liss Inc., United States (published online Oct. 2008, published in print Feb. 2009).

Tucker, T., et al., "Different patterns of mast cells distinguish diffuse from encapsulated neurofibromas in patients with neurofibromatosis I," Journal of Histochemistry and Cytochemistry 59(6):584-590, Sage Journals for Histochemical Society Inc., United States (Jun. 2011).

The United States Pharmacopeia—National Formulary (NF18), "<941> X-Ray Diffraction," 23rd Edition, DD. 1843-1844 (1995).

Florence, A. J., "Polymoiph screening in pharmaceutical development," European Pharmaceutical Review, Issue 4, accessed at URL:[https://www.europeanpharmaceuticalreview.com/article/3659/polymorph-screening-in-pharmaceutical-development/] onFeb. 14, 2022, 14 pages (Aug. 19, 2010).

International Search Report and Written Opinion for International Application No. PCT/US2021/018373, European Patent Office, Netherlands, mailed on Dec. 8, 2021, 20 pages.

International Search Report and Written Opinion for International Application No. PCT/US2021/018378, European Patent Office, Netherlands, mailed on Nov. 12, 2021, 14 pages.

International Search Report and Written Opinion for International Application No. PCT/US2021/018381, European Patent Office, Netherlands, mailed on Dec. 8, 2021, 25 pages.

* cited by examiner

DISPERSIBLE FORMULATIONS OF N-((R)-2,3-DIHYDROXYPROPOXY)-3,4-DIFLUORO-2-(2-FLUORO-4-IODO-PHENYLAMINO)-BENAZMIDE AND USES THEREOF

CROSS-REFERENCE TO RELATED APPLICATION

This application is a continuation of U.S. patent application Ser. No. 18/151,707, filed Jan. 9, 2023, which is a division of U.S. application Ser. No. 17/177,999 filed Feb. 17, 2021, each of which is incorporated by reference in its entirety herein.

FIELD OF THE INVENTION

The present disclosure relates to dispersible formulations of N—((R)-2,3-dihydroxypropoxy)-3,4-difluoro-2-(2-fluoro-4-iodo-phenylamino)-benzamide for use in administration to patients in need thereof, and methods of producing such dispersible formulations. The present disclosure further relates to dispersible formulations comprising N—((R)-2,3-dihydroxypropoxy)-3,4-difluoro-2-(2-fluoro-4-iodo-phenylamino)-benzamide; methods of producing dispersible formulations comprising N—((R)-2,3-dihydroxypropoxy)-3,4-difluoro-2-(2-fluoro-4-iodo-phenylamino)-benzamide; and methods and uses of treating a tumor, a cancer, or a Rasopathy disorder by administering N—((R)-2,3-dihydroxypropoxy)-3,4-difluoro-2-(2-fluoro-4-iodo-phenylamino)-benzamide to a subject in need thereof.

BACKGROUND

Neurofibromatosis Type 1 ("NF1") is characterized by diverse, progressive cutaneous, neurological, skeletal and neoplastic manifestations with no standard drug treatment options available. Neurofibromas are benign peripheral nerve sheath tumors comprised of a mixture of Schwann cells, fibroblasts, perineurial cells, and mast cells and occur in 20 to 50% of NF1 patients (Tucker, et al. (2011) J. Histochem. Cytochem. 59(6):584-590). When a neurofibroma extends longitudinally along a nerve and involves multiple fascicles, it is classified as a plexiform neurofibroma (PN). Plexiform neurofibromas rarely regress spontaneously, and in many patients their growth is relentless. Plexiform neurofibromas represent a major cause of morbidity and disfigurement in individuals with NF1, and when symptomatic, are associated with increased mortality (Rasmussen, et al. (2001) Am. J. Hum. Genet. 68(5): 1110-1118; Prada, et al. (2012) J. Pediat. 160(3):461-467). As tumor growth progresses, such lesions produce dysfunction, pain, and cosmetic disfigurement and can compress the airway or spinal cord. Furthermore, PNs have the potential to undergo malignant transformation producing malignant peripheral nerve sheath tumors (MPNSTs).

Previous longitudinal retrospective studies have demonstrated age dependent differences in plexiform neurofibromas, with high inverse correlation of PN growth to patient age (Dombi, et al. (2007) Neurology. 68(9):643-647; Nguyen, et al. (2012) Orphanet J. rare Dis. 7(75); Tucker, et al. (2008) Am. J. Med. Genet. 46:81-85). In a retrospective review, Tucker et al. analyzed serial MRIs of 34 patients (median 10 years of age, range 1 to 47 years) with a measurable PN for a median follow-up length of 6 years (range 1 to 15 years). This study observed that the difference between the initial and final two-dimensional estimated tumor size was significantly greater in younger individuals compared to older individuals; 3.2 $cm^2$ vs 0.2 $cm^2$, respectively ($p=0.031$). In addition, the growth rate of tumors in patients <10 years of age (0.7 $cm^2$/year) was significantly greater than that of tumors in patients >10 years of age (0.03 $cm^2$/year, $p=0.014$). Similarly, in an observational study of 49 patients 3 to 25 years of age (median 8.3 years), Dombi et al. observed that PN volume increased more rapidly than body weight over time ($p=0.026$). Furthermore, there was a tendency for patients younger than the median age of 8.3 years to have a greater increase in PN volume per year vs older children; 21.1% vs 8.4% volume change per year, respectively ($p=0.001$). This trend holds true when PN growth rate is expressed relative to the rate of increase in body size.

Based on the findings of Tucker and Dombi, Nguyen et al. conducted a retrospective study of 71 patients with an evaluable PN for a median follow-up of 2.2 years (range 1.1 to 4.9 years). The rate of growth of the individual tumors was inversely correlated with age at initial examination (Spearman's rho=−0.33, $p<0.001$), but not with the tumor volume on initial MRI examination. Also, tumors that grew more than 20% per year were significantly more frequent among children than among adults ($p<0.001$). In summation, findings from three independent retrospective reviews of PN volume clearly show that the growth rate of PNs in NF1 patients is inversely correlated with age, indicating discrete age dependent tumor differences and an unmet need in the pediatric population.

These observations suggest that the youngest patients could receive the greatest clinical benefit from therapy. However, the youngest potential patients with an urgent medical need for treatment may struggle to receive treatment due to the inability to swallow a whole capsule or tablet. Therefore, there is a need for an age-appropriate pediatric formulation that permits accurate dosing and enhanced adherence to optimize efficacy and safety in this population.

Moreover, any patient in need of treatment but who experiences difficulty swallowing ("dysphagia") would benefit from a non-capsule or tablet formulation which can be orally administered. Dysphagia can be caused by a variety of circumstances affecting one or more components of the swallowing process. These can include but are not limited to: physical damage to the tongue, pharynx, larynx, esophagus, or trachea caused by trauma, infection, proliferative disease; treatment for a such a condition; congenital anatomical defects such as cleft palate; underdevelopment at young age; weakening at old age; dementia, memory loss, or cognitive decline; or any condition which otherwise weakens or damages the muscles or nerves used in the swallowing process, such as Parkinson's disease, stroke, or nervous system disease.

N—((R)-2,3-dihydroxypropoxy)-3,4-difluoro-2-(2-fluoro-4-iodo-phenylamino)-benzamide ("mirdametinib", or "PD-0325901") is a small molecule drug which has been designed to inhibit mitogen-activated protein kinase kinase 1 ("MEK1") and mitogen-activated protein kinase kinase 2 ("MEK2"). MEK1 and MEK2 are proteins that play key roles in the mitogen-activated protein kinase ("MAPK") signaling pathway. The MAPK pathway is critical for cell survival and proliferation, and overactivation of this pathway has been shown to lead to tumor development and growth. Mirdametinib is a highly potent and specific allosteric non-ATP-competitive inhibitor of MEK1 and MEK2. By virtue of its mechanism of action, mirdametinib leads to significantly inhibited phosphorylation of the extracellular regulated MAP kinases ERK1 and ERK2, thereby leading to impaired growth of tumor cells both in vitro and in vivo. In addition, evidence indicates that inflammatory cytokineinduced increases in MEK/ERK activity contribute to the inflammation, pain, and tissue destruction associated with rheumatoid arthritis and other inflammatory diseases.

Crystal forms of N—((R)-2,3-dihydroxypropoxy)-3,4-difluoro-2-(2-fluoro-4-iodo-phenylamino)-benzamide have been described previously. WO2002/006213 describes crystalline Forms I and II, and is incorporated by reference. Form I is characterized by an XRPD containing peaks at one or more of 10.6, 13.7, 19.0, and 23.7 degrees 2θ; Form II is characterized by an XRPD containing peaks at 5.5 and/or 19.6 degrees 2θ. Form I is characterized by a melting point at about 117° C.-118° C., and Form II is characterized as melting at 89° C.-90° C., as determined by DSC.

U.S. Pat. No. 7,060,856 ("the '856 patent") describes a method of producing Form IV, and is incorporated by reference. The '856 patent indicates that the material produced by this method was greater than 90% Form IV (The '856 patent, Example 1). The '856 patent also states that the differential scanning calorimetry ("DSC") of the material produced shows an onset of melting at 110° C., as well as a small peak with an onset at 117° C., consistent with the material being a mixture of two forms. Compositions containing more than one polymorphic form are generally undesirable because of the potential of interconversion of one polymorphic form to another. Polymorphic interconversion can lead to differences in the effective dose or physical properties affecting processability of a drug, caused by differences in solubility or bioavailability.

There is a need for a dispersible formulation of N—((R)-2,3-dihydroxypropoxy)-3,4-difluoro-2-(2-fluoro-4-iodo-phenylamino)-benzamide which is safely administrable to patients who have difficulty swallowing full capsules or tablets (e.g., pediatric patients or patients suffering from dysphagia), for use in treatment of a tumor, a cancer, or a Rasopathy disorder. Given the apparent mixture of forms in previously disclosed Form IV, there is a need for dispersible formulations containing essentially pure Form IV of N—((R)-2,3-dihydroxypropoxy)-3,4-difluoro-2-(2-fluoro-4-iodo-phenylamino)-benzamide to limit polymorphic interconversion between forms which may affect solubility and bioavailability.

BRIEF SUMMARY OF THE INVENTION

The present disclosure features useful compositions for treating disorders whereby aberrant MEK1 or MEK2 activity is implicated, e.g., a tumor, a cancer, or a Rasopathy disorder, such as neurofibromatosis type 1, in a subject in need thereof. In some aspects, the methods and compositions described herein are useful in treating patients who struggle to swallow whole capsules or tablets, e.g., pediatric patients or subjects suffering from dysphagia, such as patients with esophageal cancer, Parkinson's disease, amyotrophic lateral sclerosis, stroke, achalasia, or esophageal narrowing. In some aspects, the compositions comprise Form I, Form II, or Form IV of N—((R)-2,3-dihydroxypropoxy)-3,4-difluoro-2-(2-fluoro-4-iodo-phenylamino)-benzamide.

Pharmaceutical Composition

In some aspects, the present disclosure is directed to a pharmaceutical composition comprising an amount of N—((R)-2,3-dihydroxypropoxy)-3,4-difluoro-2-(2-fluoro-4-iodo-phenylamino)-benzamide of Formula (I)

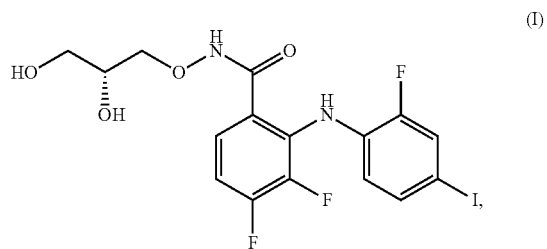 [SMILES: O=C(NOC[C@H](O)CO)c1ccc(F)c(F)c1Nc1ccc(I)cc1F]

wherein the pharmaceutical composition is dispersible in a potable liquid. (e.g., water) or orodispersible in a subject's saliva.

In some aspects, the N—((R)-2,3-dihydroxypropoxy)-3,4-difluoro-2-(2-fluoro-4-iodo-phenylamino)-benzamide in the pharmaceutical compositions described herein is crystalline. In some aspects, the crystalline form of N—((R)-2,3-dihydroxypropoxy)-3,4-difluoro-2-(2-fluoro-4-iodo-phenylamino)-benzamide is selected from the group consisting of: (a) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 7.3±0.2, and 14.6±0.2 degrees two theta; (b) a crystalline form of N—((R)-2,3-dihydroxypropoxy)-3,4-difluoro-2-(2-fluoro-4-iodo-phenylamino)-benzamide characterized by an XRPD pattern having peaks at 10.6±0.2, 13.7±0.2, 19.0±0.2, and 23.7±0.2 degrees two theta; and (c) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2 and 19.6±0.2 degrees two theta.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 7.3±0.2, and 14.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 7.3±0.2, 14.6±0.2, and 25.0±0.2 degrees two theta.

Figure 1A:
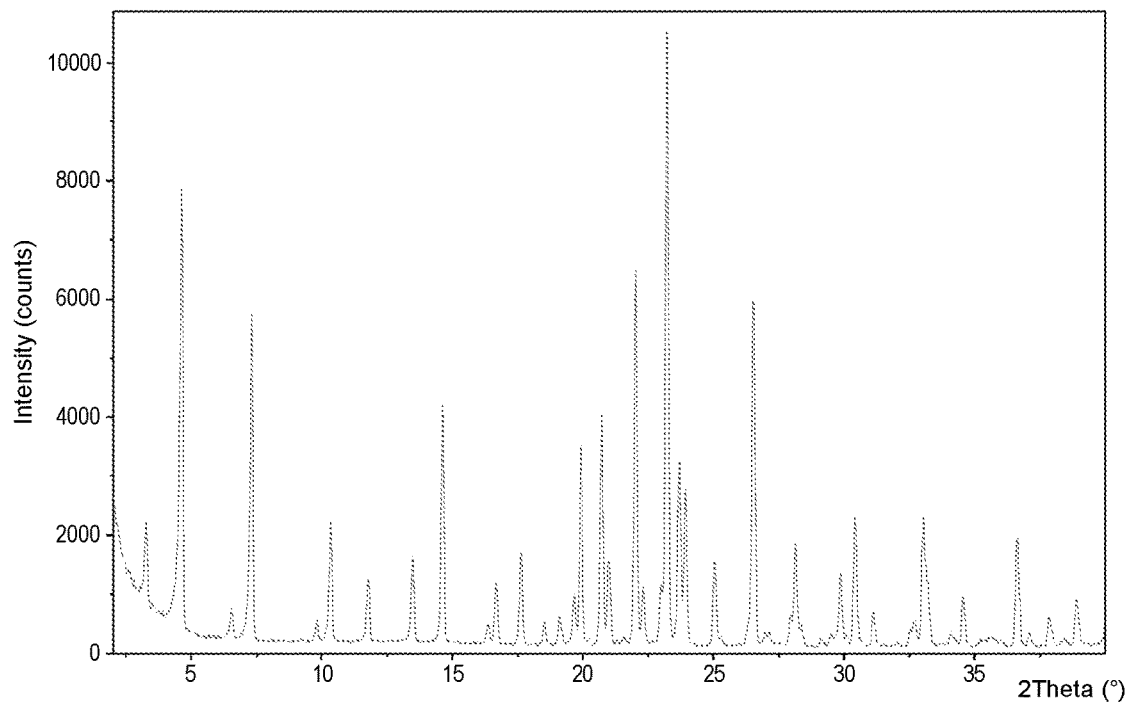
FIG. 1A is a X-ray powder diffraction pattern ("XRPD") corresponding to essentially pure crystalline Form IV of N—((R)-2,3-dihydroxypropoxy)-3,4-difluoro-2-(2-fluoro-4-iodo-phenylamino)-benzamide.

In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 1A.

In some aspects, the crystalline form of N—((R)-2,3-dihydroxypropoxy)-3,4-difluoro-2-(2-fluoro-4-iodo-phenylamino)-benzamide is characterized by a DSC profile which does not include an endotherm with an onset at about 117° C.

Figure 1B:
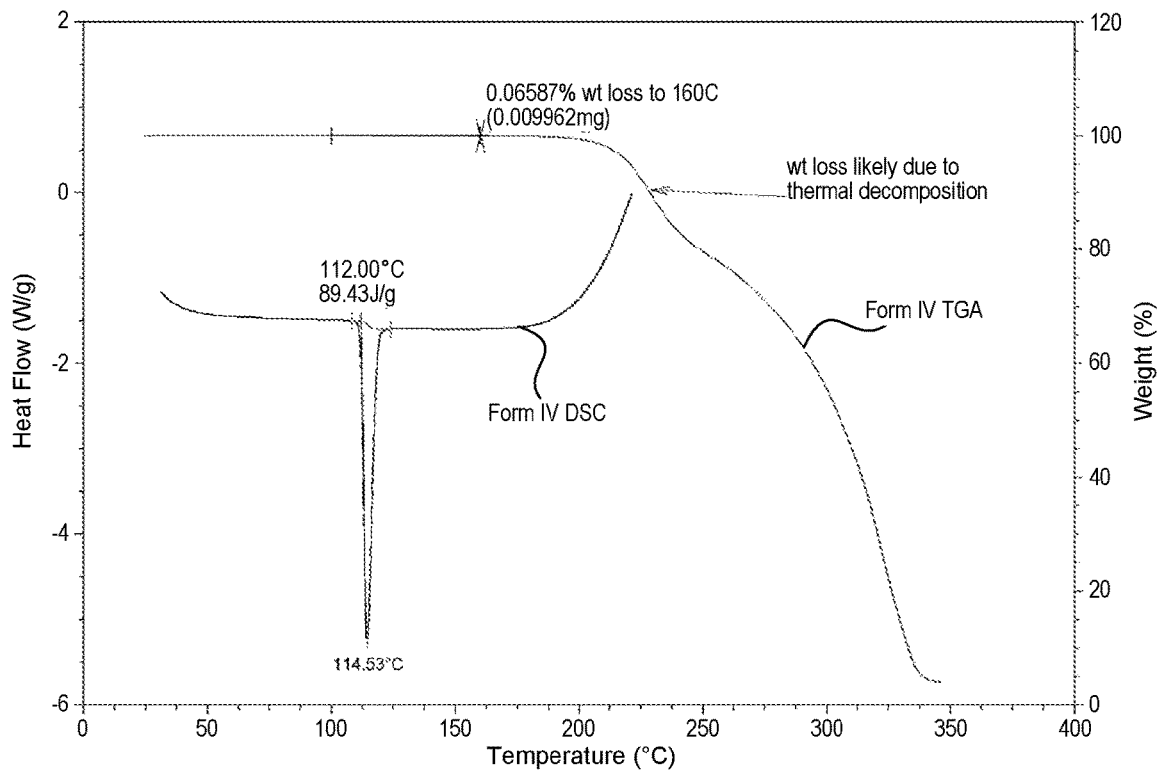
FIG. 1B is a thermogravimetric analysis thermogram ("TGA") and a differential scanning calorimetry thermogram ("DSC") corresponding to essentially pure crystalline Form IV of N—((R)-2,3-dihydroxypropoxy)-3,4-difluoro-2-(2-fluoro-4-iodo-phenylamino)-benzamide.
Figure 2:
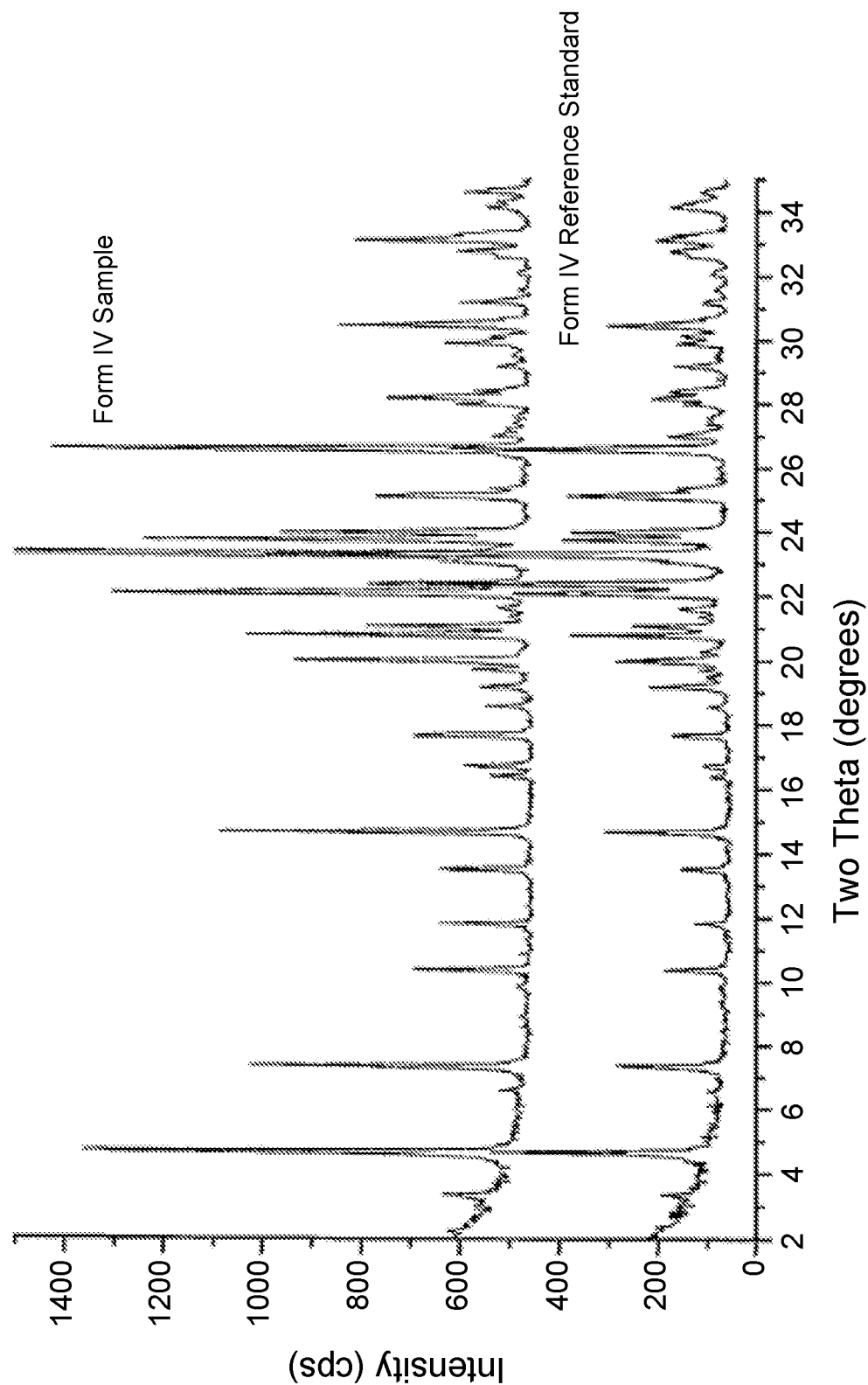
FIG. 2 is an XRPD corresponding to a batch of essentially pure Form IV of N—((R)-2,3-dihydroxypropoxy)-3,4-difluoro-2-(2-fluoro-4-iodo-phenylamino)-benzamide as initially prepared and an XRPD of a known reference standard of Form IV.
Figure 3A:
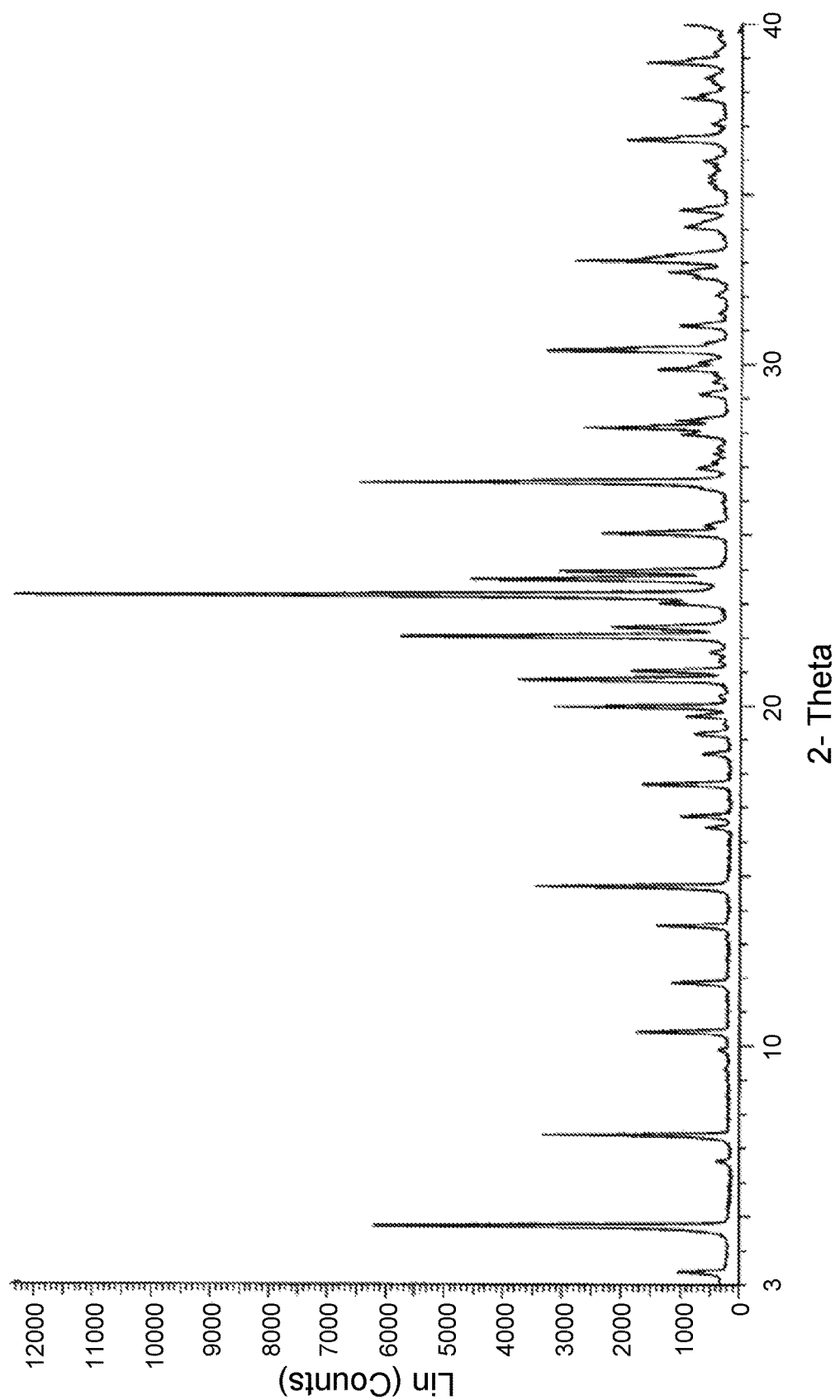
FIG. 3A is an XRPD corresponding to essentially pure Form IV of N—((R)-2,3-dihydroxypropoxy)-3,4-difluoro-2-(2-fluoro-4-iodo-phenylamino)-benzamide after storage for 68 months after production at 25° C. and ≤65% relative humidity.
Figure 3B:
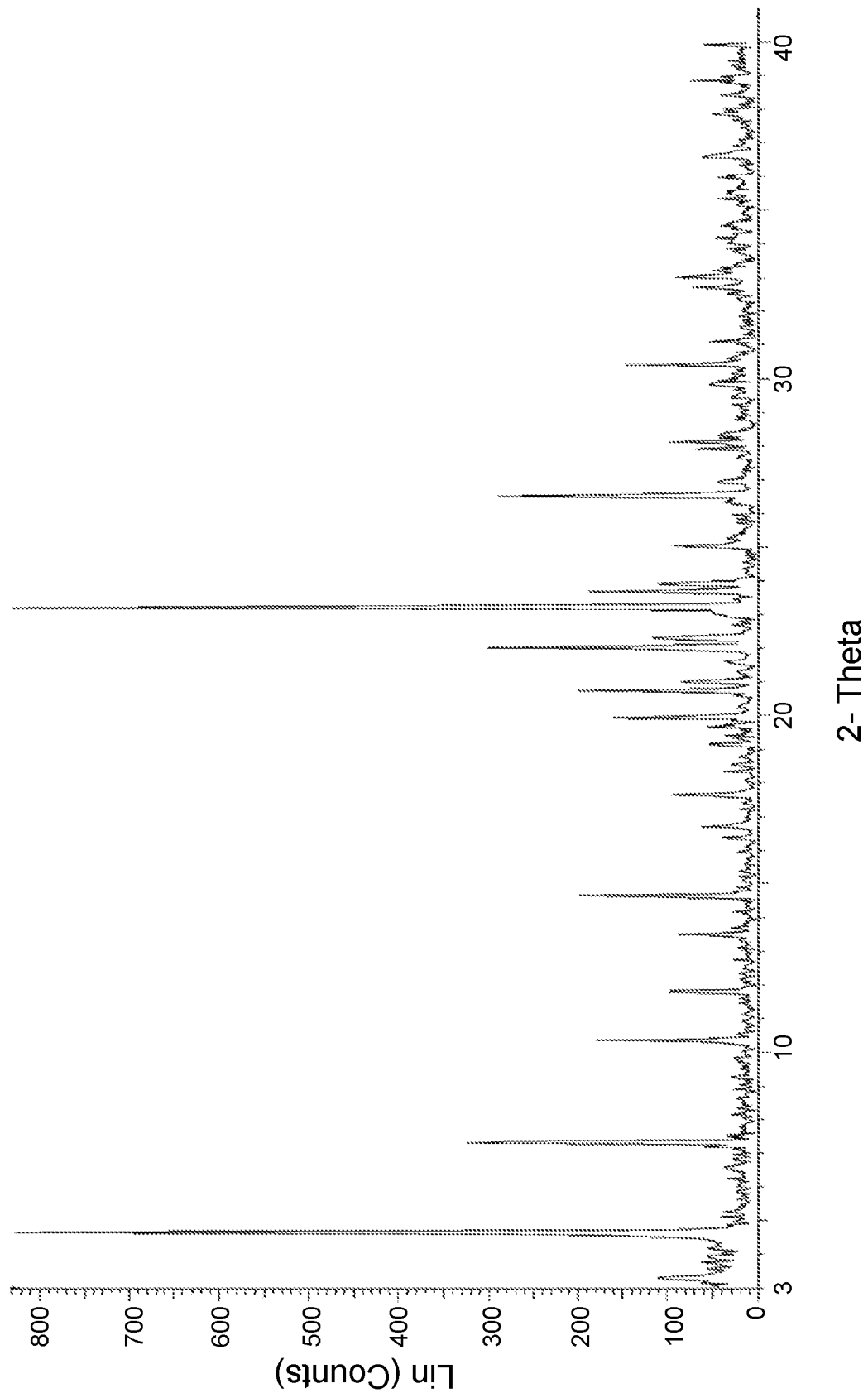
FIG. 3B is an XRPD corresponding to essentially pure Form IV of N—((R)-2,3-dihydroxypropoxy)-3,4-difluoro-2-(2-fluoro-4-iodo-phenylamino)-benzamide after storage for 140 months after production at 25° C. and ≤65% relative humidity.

In some aspects, the crystalline form of N—((R)-2,3-dihydroxypropoxy)-3,4-difluoro-2-(2-fluoro-4-iodo-phenylamino)-benzamide is characterized by one or both of: (a) a TGA profile substantially as shown in FIG. 1B; and/or (b) a DSC profile substantially as shown in FIG. 1B.

In some aspects, the crystalline form of N—((R)-2,3-dihydroxypropoxy)-3,4-difluoro-2-(2-fluoro-4-iodo-phenylamino)-benzamide does not contain any amount of Form I or Form II detectable by XRPD and/or DSC.

In some aspects, the crystalline form N—((R)-2,3-dihydroxypropoxy)-3,4-difluoro-2-(2-fluoro-4-iodo-phenylamino)-benzamide is anhydrous.

In some aspects, the crystalline form N—((R)-2,3-dihydroxypropoxy)-3,4-difluoro-2-(2-fluoro-4-iodo-phenylamino)-benzamide is Form IV. In some aspects, the crystalline form of N—((R)-2,3-dihydroxypropoxy)-3,4-difluoro-2-(2-fluoro-4-iodo-phenylamino)-benzamide is essentially pure Form IV.

In some aspects, the essentially pure Form IV of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 3 months at standard warehouse conditions (15° C.-25° C. and ≤65% relative humidity). In some aspects, the essentially pure Form IV of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 6 months at standard warehouse conditions (15° C.-25° C. and ≤65% relative humidity). In some aspects, the essentially pure Form IV of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 1 year at standard warehouse conditions (15° C.-25° C. and ≤65% relative humidity). In some aspects, the essentially pure Form IV of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 68 months at standard warehouse conditions (15° C.-25° C. and ≤65% relative humidity). In some aspects, the essentially pure Form IV of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for ≥140 months at standard warehouse conditions (15° C.-25° C. and ≤65% relative humidity). In some aspects, the essentially pure Form IV of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for ≥14 years at standard warehouse conditions (15° C.-25° C. and ≤65% relative humidity).

In some aspects, the XRPD pattern is generated using a PANALYTICAL® X'Pert Pro diffractometer using Ni-filtered Cu Kα (45 kV/40 mA) radiation and a step size of 0.03° 2θ with a X'CELERATOR® Real Time Multi-Strip detector, configured (a) on the incidental beam side as follows: variable divergence slits (10 mm irradiated length), 0.04 rad Soller slits, fixed anti-scatter slit (0.50°), and 10 mm beam mask, and (b) on the diffracted beam side as follows: variable anti-scatter slit (10 mm observed length) and 0.04 rad Soller slit or a BRUKER® D8® ADVANCE™ system using Cu Kα (40 kV/40 mA) radiation and a step size of 0.03° 2θ with a LYNXEYE™ detector, configured (a) on the incidental beam side as follows: Goebel mirror, mirror exit slit (0.2 mm), 2.5° Soller slit, beam knife, and (b) on the diffracted beam side as follows: anti-scatter slit (8 mm) and 2.5° Soller slit; wherein samples are mounted flat on zero-background Si wafers. In some aspects, the DSC pattern is generated using a TA Instruments Q100 or Q2000 differential scanning calorimeter at a rate of temperature increase of about 15° C./min.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.6±0.2, 13.7±0.2, 19.0±0.2, and 23.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.6±0.2, 13.7±0.2, 14.6±0.2, 17.3±0.2, 18.0±0.2, 18.2±0.2, 19.0±0.2, 19.3±0.2, 20.1±0.2, 21.0±0.2, 21.9±0.2, 22.4±0.2, 23.7±0.2, 24.0±0.2, 24.9±0.2, 26.3±0.2, 27.6±0.2, 28.0±0.2, 30.1±0.2, 32.1±0.2, 32.3±0.2, 32.9±0.2, 35.8±0.2, and 37.7±0.2 degrees two theta.

In some aspects, the crystalline form N—((R)-2,3-dihydroxypropoxy)-3,4-difluoro-2-(2-fluoro-4-iodo-phenylamino)-benzamide is characterized by a DSC profile with an endotherm with onset at about 117° C.

In some aspects, the crystalline form N—((R)-2,3-dihydroxypropoxy)-3,4-difluoro-2-(2-fluoro-4-iodo-phenylamino)-benzamide is Form I.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2 and 19.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 10.7±0.2, 16.5±0.2, 19.6±0.2, 22.0±0.2, 22.5±0.2, 23.6±0.2, 24.1±0.2, 25.0±0.2, 26.2±0.2, 27.6±0.2, 29.1±0.2, 30.5±0.2, 31.7±0.2, 33.3±0.2, and 39.0±0.2 degrees two theta.

In some aspects, the crystalline form of N—((R)-2,3-dihydroxypropoxy)-3,4-difluoro-2-(2-fluoro-4-iodo-phenylamino)-benzamide is characterized by a DSC profile with an endotherm with onset at about 87° C.

In some aspects, the crystalline form of N—((R)-2,3-dihydroxypropoxy)-3,4-difluoro-2-(2-fluoro-4-iodo-phenylamino)-benzamide is Form II.

In some aspects, the pharmaceutical composition further comprises one or more pharmaceutically acceptable carriers.

In some aspects, the pharmaceutical composition is for oral administration. In some aspects, the pharmaceutical composition is dispersible. In some aspects, the pharmaceutical composition is orodispersible.

In some aspects, the pharmaceutical composition is a tablet, a powder, granules, minitablets, or pellets (also called beads).

In some aspects, the pharmaceutical composition is a powder. In some aspects, the pharmaceutical composition is a dispersible powder. In some aspects, a capsule or sachet comprises the dispersible powder.

In some aspects, the pharmaceutical composition is in the form of granules. In some aspects, the granules are dispersible granules. In some aspects, a capsule or sachet comprises the dispersible granules.

In some aspects, the pharmaceutical composition is in the form of minitablets. In some aspects, the minitablets are dispersible minitablets. In some aspects, a capsule or sachet comprises the dispersible minitablets.

In some aspects, the pharmaceutical composition is in the form of pellets. In some aspects, the pellets are dispersible pellets. In some aspects, a capsule or sachet comprises the dispersible pellets.

In some aspects, the pharmaceutical composition is a tablet. In some aspects, the tablet is a dispersible tablet. In some aspects, the tablet is an orodispersible tablet.

In some aspects, the pharmaceutical composition that is a dispersible tablet, dispersible powder, dispersible granules, dispersible minitablets, or dispersible pellets comprises about 0.1 mg to about 20 mg of N—((R)-2,3-dihydroxypropoxy)-3,4-difluoro-2-(2-fluoro-4-iodo-phenylamino)-benzamide, wherein each component of the pharmaceutical composition is as follows: (a) about 0.1 wt/wt % to about 7 wt/wt % of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pharmaceutical composition that is a dispersible tablet, dispersible powder, dispersible granules, dispersible minitablets, or dispersible pellets comprises about 0.1 mg to about 20 mg of N—((R)-2,3-dihydroxypropoxy)-3,4-difluoro-2-(2-fluoro-4-iodo-phenylamino)-benzamide, wherein each component of the pharmaceutical composition is as follows: (a) about 0.2 wt/wt % to about 1.5 wt/wt % of N—((R)-2,3-dihydroxypropoxy)-3,4-difluoro-2-(2-fluoro-4-iodo-phenylamino)-benzamide; (b) about 75 wt/wt % to about 98 wt/wt % of one or more diluents; (c) about 3 wt/wt % to about 8 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pharmaceutical composition that is a dispersible tablet, dispersible powder, dispersible granules, dispersible minitablets, or dispersible pellets comprises about 0.1 mg to about 20 mg of N—((R)-2,3-dihydroxypropoxy)-3,4-difluoro-2-(2-fluoro-4-iodo-phenylamino)-benzamide, wherein each component of the pharmaceutical composition is as follows: (a) about 0.5 wt/wt % to about 1.2 wt/wt % of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pharmaceutical composition that is a dispersible tablet, dispersible powder, dispersible granules, dispersible minitablets, or dispersible pellets comprises about 0.5 mg of N—((R)-2,3-dihydroxypropoxy)-3,4-difluoro-2-(2-fluoro-4-iodo-phenylamino)-benzamide. In some aspects, the pharmaceutical composition comprises about 1 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 2 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 3 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 4 mg of N—((R)-2,3-dihydroxypropoxy)-3,4-difluoro-2-(2-fluoro-4-iodo-phenylamino)-benzamide.

In some aspects, at least one of the diluents is selected from the group consisting of microcrystalline cellulose, lactose, mannitol, sorbitol, xylitol, sucrose, starch, pregelatinized starch, calcium sulfate, calcium carbonate and dibasic calcium phosphate. In some aspects, at least one of the diluents is microcrystalline cellulose.

In some aspects, at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid. In some aspects, at least one of the disintegrants is croscarmellose sodium.

In some aspects, at least one of the flavoring agents is selected from the group consisting of natural or synthetic flavors including but not limited to, grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring. In some aspects, at least one of the flavoring agents is grape flavoring.

In some aspects, at least one of the sweeteners is selected from the group consisting of sucralose, acesulfame, saccharin, sucrose, xylitol, mannitol, sorbitol, glucose, fructose, and aspartame. In some aspects, at least one of the sweeteners is sucralose.

In some aspects, at least one of the lubricants is selected from the group consisting of magnesium stearate, stearic acid, calcium stearate, zinc stearate, beeswax, colloidal silicon dioxide, hydrogenated vegetable oil, sodium stearyl fumarate, glycerol dibehenate, and talc. In some aspects, at least one of the lubricants is magnesium stearate.

Methods of Treatment

In some aspects, the present disclosure provides a method of treating a tumor, a cancer, or a Rasopathy disorder comprising administering to a subject in need of such treatment a pharmaceutical composition (e.g., a dispersible tablet, a dispersible powder, dispersible granules, dispersible mintablets, or dispersible pellets) described herein.

In some aspects, the present disclosure provides use of a pharmaceutical composition (e.g., a dispersible tablet, a dispersible powder, dispersible granules, dispersible minitablets, or dispersible pellets) described herein for the manufacture of a medicament for treating a tumor, a cancer, or a Rasopathy disorder.

In some aspects, the tumor is a neurofibroma. In some aspects, the tumor is a neurofibroma associated with Neurofibromatosis Type 1. In some aspects, the tumor is selected from the group consisting of cutaneous neurofibroma, plexiform neurofibroma, optic pathway glioma, low-grade glioma, high-grade glioma, or malignant peripheral nerve sheath tumor. In some aspects, the tumor is plexiform neurofibroma.

In some aspects, the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

In some aspects, the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum. In some aspects, the leukemia is selected from the group consisting of acute lymphocytic leukemia, acute myelogenous leukemia, chronic lymphocytic leukemia, and chronic myelogenous leukemia. In some aspects, the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia. In some aspects, the lung cancer is selected from the group consisting of lung adenocarcinoma, squamous non-small cell lung cancer, non-squamous non-small cell lung cancer, and small cell lung cancer.

In some aspects, the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

In some aspects, an individual dose of the N—((R)-2,3-dihydroxypropoxy)-3,4-difluoro-2-(2-fluoro-4-iodo-phenylamino)-benzamide is administered as more than one dispersible tablet, more than one dose of dispersible powder, more than one dose of dispersible granules, more than one dose of dispersible minitablets, more than one dose of dispersible pellets, or a combination thereof. For example, a dose of 3 mg of the N—((R)-2,3-dihydroxypropoxy)-3,4-difluoro-2-(2-fluoro-4-iodo-phenylamino)-benzamide can be administered as two dispersible tablets—one containing 2 mg and the other containing 1 mg or as three dispersible tablets each containing 1 mg. As another example, a dose of 1.5 mg of the N—((R)-2,3-dihydroxypropoxy)-3,4-difluoro-2-(2-fluoro-4-iodo-phenylamino)-benzamide can be administered as two dispersible dosage forms—one dispersible tablet containing 1 mg and a separate unit of dispersible powder containing 0.5 mg or as three units of dispersible powder each containing 0.5 mg.

In some aspects, the N—((R)-2,3-dihydroxypropoxy)-3,4-difluoro-2-(2-fluoro-4-iodo-phenylamino)-benzamide is administered in a total daily dose that does not exceed 20 mg. In some aspects, the N—((R)-2,3-dihydroxypropoxy)-3,4-difluoro-2-(2-fluoro-4-iodo-phenylamino)-benzamide is administered in a total daily dose that does not exceed 10 mg. In some aspects, the N—((R)-2,3-dihydroxypropoxy)-3,4-difluoro-2-(2-fluoro-4-iodo-phenylamino)-benzamide is administered in a total daily dose that does not exceed 8 mg. In some aspects, the N—((R)-2,3-dihydroxypropoxy)-3,4-difluoro-2-(2-fluoro-4-iodo-phenylamino)-benzamide is administered in a total daily dose that does not exceed 6 mg. In some aspects, the N—((R)-2,3-dihydroxypropoxy)-3,4-difluoro-2-(2-fluoro-4-iodo-phenylamino)-benzamide is administered in a total daily dose that does not exceed 2 mg. In some aspects, the N—((R)-2,3-dihydroxypropoxy)-3,4-difluoro-2-(2-fluoro-4-iodo-phenylamino)-benzamide is administered in a total daily dose that does not exceed 1 mg.

In some aspects, the N—((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising (a) 21 consecutive days in which the total daily dose is administered; followed by (b) 7 consecutive days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising (a) three 7-day periods each comprising (i) 5 days in which the total daily dose is administered and (ii) 2 days in which no N—((R)-2,3-dihydroxypropoxy)-3,4-difluoro-2-(2-fluoro-4-iodo-phenylamino)-benzamide; and (b) 7 days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising (a) three 7-day periods each comprising (i) 5 consecutive days in which the total daily dose is administered and (ii) 2 consecutive days in which no N—((R)-2,3-dihydroxypropoxy)-3,4-difluoro-2-(2-fluoro-4-iodo-phenylamino)-benzamide; followed by (b) 7 consecutive days in which no N—((R)-2,3-dihydroxypropoxy)-3,4-difluoro-2-(2-fluoro-4-iodo-phenylamino)-benzamide is administered.

In some aspects, the 28-day dosing cycle is repeated up to a total of 24 consecutive 28-day dosing cycles.

In some aspects, the N—((R)-2,3-dihydroxypropoxy)-3,4-difluoro-2-(2-fluoro-4-iodo-phenylamino)-benzamide is administered on a 28-day dosing cycle comprising 28 days in which the total daily dose is administered.

In some aspects, the subject experiences dysphagia. In some aspects, the subject experiences dysphagia caused by one or more of: disease of the nervous system, muscle weakening, developmental disability, stroke, injury, anatomical defect, cancer, treatment for cancer, allergic reaction, dementia, memory loss, or cognitive decline.

In some aspects, the subject is a pediatric subject.

In some aspects, the total daily dose of N—((R)-2,3-dihydroxypropoxy)-3,4-difluoro-2-(2-fluoro-4-iodo-phenylamino)-benzamide is administered two times daily. In some aspects, the total daily dose of the N—((R)-2,3-dihydroxypropoxy)-3,4-difluoro-2-(2-fluoro-4-iodo-phenylamino)-benzamide is administered two times daily at a dose of about 0.1 mg to about 10 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 0.25 mg each. In some aspects, the total daily dose of the N—((R)-

2,3-dihydroxypropoxy)-3,4-difluoro-2-(2-fluoro-4-iodo-phenylamino)-benzamide is administered two times daily at a dose of about 0.5 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 1 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 2 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 4 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 5 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 10 mg each.

In some aspects, the total daily dose of the N—((R)-2,3-dihydroxypropoxy)-3,4-difluoro-2-(2-fluoro-4-iodo-phenylamino)-benzamide is administered once daily. In some aspects, the total daily dose of the N—((R)-2,3-dihydroxypropoxy)-3,4-difluoro-2-(2-fluoro-4-iodo-phenylamino)-benzamide is administered once daily at a dose of about 0.1 mg to about 20 mg. In some aspects, the total daily dose of the N—((R)-2,3-dihydroxypropoxy)-3,4-difluoro-2-(2-fluoro-4-iodo-phenylamino)-benzamide is administered once daily at a dose of about 0.5 mg. In some aspects, the total daily dose of the N—((R)-2,3-dihydroxypropoxy)-3,4-difluoro-2-(2-fluoro-4-iodo-phenylamino)-benzamide is administered once daily at a dose of about 1 mg. In some aspects, the total daily dose of the N—((R)-2,3-dihydroxypropoxy)-3,4-difluoro-2-(2-fluoro-4-iodo-phenylamino)-benzamide is administered once daily at a dose of about 2 mg. In some aspects, the total daily dose of the N—((R)-2,3-dihydroxypropoxy)-3,4-difluoro-2-(2-fluoro-4-iodo-phenylamino)-benzamide is administered once daily at a dose of about 4 mg. In some aspects, the total daily dose of the N—((R)-2,3-dihydroxypropoxy)-3,4-difluoro-2-(2-fluoro-4-iodo-phenylamino)-benzamide is administered once daily at a dose of about 8 mg. In some aspects, the total daily dose of the N—((R)-2,3-dihydroxypropoxy)-3,4-difluoro-2-(2-fluoro-4-iodo-phenylamino)-benzamide is administered once daily at a dose of about 10 mg. In some aspects, the total daily dose of the N—((R)-2,3-dihydroxypropoxy)-3,4-difluoro-2-(2-fluoro-4-iodo-phenylamino)-benzamide is administered once daily at a dose of about 20 mg.

In some aspects, the N—((R)-2,3-dihydroxypropoxy)-3,4-difluoro-2-(2-fluoro-4-iodo-phenylamino)-benzamide is administered in a total daily dose that does not exceed 20 mg. In some aspects, the N—((R)-2,3-dihydroxypropoxy)-3,4-difluoro-2-(2-fluoro-4-iodo-phenylamino)-benzamide is administered in a total daily dose that does not exceed 10 mg. In some aspects, the N—((R)-2,3-dihydroxypropoxy)-3,4-difluoro-2-(2-fluoro-4-iodo-phenylamino)-benzamide is administered in a total daily dose that does not exceed 8 mg. In some aspects, the N—((R)-2,3-dihydroxypropoxy)-3,4-difluoro-2-(2-fluoro-4-iodo-phenylamino)-benzamide is administered in a total daily dose that does not exceed 6 mg. In some aspects, the N—((R)-2,3-dihydroxypropoxy)-3,4-difluoro-2-(2-fluoro-4-iodo-phenylamino)-benzamide is administered in a total daily dose that does not exceed 4 mg. In some aspects, the N—((R)-2,3-dihydroxypropoxy)-3,4-difluoro-2-(2-fluoro-4-iodo-phenylamino)-benzamide is administered in a total daily dose that does not exceed 2 mg. In some aspects, the N—((R)-2,3-dihydroxypropoxy)-3,4-difluoro-2-(2-fluoro-4-iodo-phenylamino)-benzamide is administered in a total daily dose that does not exceed 1 mg.

Method of Manufacturing a Pharmaceutical Composition

In some aspects, the present disclosure provides a method of manufacturing a pharmaceutical composition, the method comprising forming a pharmaceutical composition described herein.

Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "mirdametinib" and "PD-0325901" refer to the single enantiomer N—((R)-2,3-dihydroxypropoxy)-3,4-difluoro-2-(2-fluoro-4-iodo-phenylamino)-benzamide.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The term "pediatric" refers to a human subject under the age of 21 years at the time of treatment. The term "pediatric" can be further divided into various subpopulations including: neonates (from birth through the first 28 days of life); infants (29 days of age to less than two years of age); children (two years of age to less than 12 years of age); and adolescents (12 years of age through 21 years of age (up to, but not including, the twenty-second birthday)). See, e.g., Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994. Younger pediatric patients in particular, such as neonates, infants and young children, can have difficulty swallowing whole capsules or tablets.

The term "dispersible" as used herein refers to a composition (e.g., a tablet, powder, granules, minitablets, or pellets) which disintegrates and/or dissolves when combined with water or another potable liquid (e.g., a non-water beverage), or a subject's own saliva when placed in the subject's mouth, with or without the addition of agitation or temperature modification. In some aspects, the dispersible composition disintegrates or dissolves within 10 minutes, 9 minutes, 8 minutes, 7 minutes, 6 minutes, 5 minutes, 4 minutes, 3 minutes, 2 minutes, or 1 minute after being combined with water or another potable liquid. Such disintegration or dissolution need not be complete. For example, a dispersible tablet may dissolve almost entirely, but some undissolved particulate matter may remain.

The term "orodispersible" refers to a composition which is capable of dissolving or disintegrating in a subject's mouth (i.e., dissolving or disintegrating in a subject's saliva) if administered orally, without a requirement of first dissolving or disintegrating in a separate container.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

In certain aspects, a subject is successfully "treated" for a tumor, according to the methods described herein if the patient shows one or more of the following: a reduction in the size of the tumor; relief of one or more symptoms associated with the specific tumor; a reduction in the volume of the tumor; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given tumor can be used to determine whether an effective amount of mirdametinib meets any of these particular endpoints (e.g., CR, PFS, PR).

In certain aspects, a subject is successfully "treated" for cancer, e.g., lung cancer or ovarian cancer, according to the methods described herein if the patient shows one or more of the following: a reduction in the number of or complete absence of cancer cells; relief of one or more symptoms associated with the specific cancer; reduced morbidity and mortality; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given cancer can be used to determine whether an effective amount of mirdametinib meets any of these particular endpoints (e.g., CR, PFS, PR).

The terms "pharmaceutically acceptable carrier," "pharmaceutically acceptable excipient," "physiologically acceptable carrier," or "physiologically acceptable excipient" refer to a pharmaceutically acceptable material, composition, or vehicle, such as a liquid or solid excipient, solvent, or encapsulating material. In one aspect, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy,* 21$^{st}$ Edition, Lippincott Williams & Wilkins: Philadelphia, PA, 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3$^{rd}$ Edition, Ash and Ash Eds., Gower Publishing Company: 2007; Pharmaceutical Preformulation and Formulation, Gibson Ed., CRC Press LLC: Boca Raton, FL, 2004 (incorporated herein by reference). Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, calcium sulfate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The term "pharmaceutical composition," as used herein, represents a composition containing a compound described herein formulated with a pharmaceutically acceptable excipient or a combination of multiple pharmaceutically acceptable excipients, and can be manufactured or sold with the approval of a governmental regulatory agency as part of a therapeutic regimen for the treatment of disease in a mammal. Pharmaceutical compositions can be formulated, for example, for oral administration in unit dosage form (e.g., a tablet (e.g., dispersible tablet), powder (e.g., dispersible powder) capsule, granules, minitablets, pellets, caplet, gelcap, or syrup).

The terms "about" or "approximately" means within a range of an acceptable error for a particular value as determined by one of ordinary skill in the art, which depends in part on how the value is measured or determined. In some aspects, the term "about" or "approximately" means within 1, 2, 3, or 4 standard deviations. In some aspects, the term "about" or "approximately" means a quantity, level, value, number, frequency, percentage, dimension, size, amount, weight or length that varies by as much as 30, 25, 20, 15, 10, 9, 8, 7, 6, 5, 4, 3, 2, or 1% to a reference quantity, level, value, number, frequency, percentage, dimension, size, amount, weight or length.

As used herein, the term "administration" refers to the administration of a composition (e.g., a compound or a preparation that includes a compound as described herein) to a subject or system. Administration to an animal subject (e.g., to a human) can be by any appropriate route, such as one described herein.

The term "crystalline," as used herein, refers to a solid state form which consists of orderly arrangement of structural units. Different crystalline forms of the same compound, or a salt, hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility. See, e.g., *Remington's Pharmaceutical Sciences*, 18$^{th}$ ed., Mack Publishing, Easton PA, 173 (1990); *The United States Pharmacopeia*, 23$^{rd}$ ed., 1843-1844 (1995) (incorporated herein by reference).

Crystalline forms are commonly characterized by X-ray powder diffraction (XRPD). An XRPD pattern of reflections (peaks, typically expressed in degrees 2-theta) is commonly considered a fingerprint of a particular crystalline form. The relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings. In some instances, any particular peak in an XRPD pattern may appear as a singlet, doublet, triplet, quartet, or multiplet, depending on the type of instrument or the settings, the sensitivity of the instrument, measuring conditions, and/or purity of the crystalline form. In some instances, any particular peak in an XRPD may appear in a symmetric shape or in an asymmetric shape, e.g., having a shoulder. Moreover, instrument variation and other factors can affect the 2-theta values. A skilled artisan understanding these variations is capable of discriminating or ascertaining the defining features or characteristics of a particular crystal form using XRPD, as well as using other known physicochemical techniques.

The term "anhydrate" as applied to a compound refers to a crystalline form wherein the compound contains no structural water within the crystal lattice.

As used herein, the term "essentially pure" with respect to Form IV means that the composition comprising Form IV contains no detectable amount of another polymorphic form (e.g., Form I or Form II), as determined by observing no detectable differences in an XRPD and/or DSC pattern between a single Form IV crystal and the crystalline composition of N—((R)-2,3-dihydroxypropoxy)-3,4-difluoro-2-(2-fluoro-4-iodo-phenylamino)-benzamide. However, "essentially pure" Form IV of N—((R)-2,3-dihydroxypropoxy)-3,4-difluoro-2-(2-fluoro-4-iodo-phenylamino)-benzamide can include impurities, such as, but not limited to, synthetic reactants or by-products generated during the chemical synthesis.

As used herein, the term "aberration" as applied to a gene refers to a mutation, chromosomal loss or fusion, epigenetic chemical modification, or other event which alters the sequence, level of expression, or processed mRNA sequence associated with a gene relative to the sequence, level of expression, or processed mRNA sequence associated with the wild-type gene.

It is understood that wherever aspects are described herein with the language "comprising," otherwise analogous aspects described in terms of "consisting of" and/or "consisting essentially of" are also provided.

The details of one or more aspects are set forth in the description below. Other features, objects, and advantages will be apparent from the description and from the claims.

DETAILED DESCRIPTION OF THE INVENTION

Dispersible formulations (e.g., dispersible tablets, dispersible powders, dispersible granules, dispersible minitablets, or dispersible pellets) of N—((R)-2,3-dihydroxypropoxy)-3,4-difluoro-2-(2-fluoro-4-iodo-phenylamino)-benzamide which are safely administrable to a patient who has difficulty swallowing (e.g., a pediatric patient or a patient suffering from dysphagia) are described herein.

As with all pharmaceutical compounds and compositions, the chemical and physical properties of N—((R)-2,3-dihydroxypropoxy)-3,4-difluoro-2-(2-fluoro-4-iodo-phenylamino)-benzamide are important in its commercial development. These properties include, but are not limited to: (1) packing properties such as molar volume, bulk density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactibility, handling, flow and blend; and (6) filtration properties. These properties can affect, for example, the processing and storage of the compound and pharmaceutical compositions comprising the compound. In some aspects, N—((R)-2,3-dihydroxypropoxy)-3,4-difluoro-2-(2-fluoro-4-iodo-phenylamino)-benzamide is administered as Form I, Form II, or Form IV (e.g., essentially pure Form IV) of N—((R)-2,3-dihydroxypropoxy)-3,4-difluoro-2-(2-fluoro-4-iodo-phenylamino)-benzamide in addition to pharmaceutically acceptable carriers or excipients.

Pharmaceutical Composition

In some aspects, the present disclosure provides a pharmaceutical composition comprising an amount of N—((R)-2,3-dihydroxypropoxy)-3,4-difluoro-2-(2-fluoro-4-iodo-phenylamino)-benzamide of Formula (I)

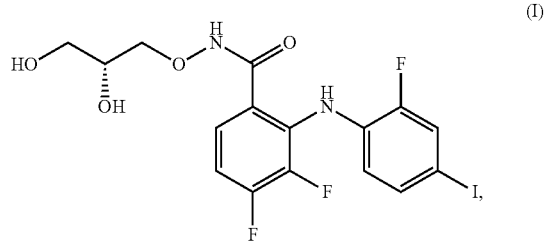 [SMILES: O=C(NOC[C@H](O)CO)c1ccc(F)c(F)c1Nc1ccc(I)cc1F]

wherein the pharmaceutical composition is dispersible in a potable liquid (e.g., water) or orodispersible in a subject's saliva.

In some aspects, the N—((R)-2,3-dihydroxypropoxy)-3,4-difluoro-2-(2-fluoro-4-iodo-phenylamino)-benzamide included in the pharmaceutical compositions described herein is crystalline. In some aspects, the crystalline form of N—((R)-2,3-dihydroxypropoxy)-3,4-difluoro-2-(2-fluoro-4-iodo-phenylamino)-benzamide is selected from the group consisting of: (a) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 7.3±0.2, and 14.6±0.2 degrees two theta; (b) a crystalline form of N—((R)-2,3-dihydroxypropoxy)-3,4-difluoro-2-(2-fluoro-4-iodo-phenylamino)-benzamide characterized by an XRPD pattern having peaks at 10.6±0.2, 13.7±0.2, 19.0±0.2, and 23.7±0.2 degrees two theta; and (c) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2 and 19.6±0.2 degrees two theta.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is characterized by an XRPD pattern having peaks at 4.6±0.2, 7.3±0.2, and 14.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 7.3±0.2, 14.6±0.2, and 25.0±0.2 degrees two theta.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is characterized by an XRPD pattern substantially as shown in FIG. 1A.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is characterized by one or both of: (a) a TGA profile substantially as shown in FIG. 1B; and/or (b) a DSC profile substantially as shown in FIG. 1B.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is characterized by a DSC profile which does not include an endotherm with an onset at about 117° C.

In some aspects, the crystalline form of N—((R)-2,3-dihydroxypropoxy)-3,4-difluoro-2-(2-fluoro-4-iodo-phenylamino)-benzamide included in the pharmaceutical compositions described herein does not contain any amount of Form I or Form II detectable by XRPD and/or DSC.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is anhydrous.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is Form IV. In some aspects, the crystalline form of of N—((R)-2,3-dihydroxypropoxy)-3,4-difluoro-2-(2-fluoro-4-iodo-phenylamino)-benzamide is essentially pure Form IV.

In some aspects, the crystalline Form IV composition included in the pharmaceutical compositions described herein is stable, as demonstrated by a substantially unchanged XRPD pattern and/or DSC profile over time. In some aspects, the crystalline Form IV composition exhibits an XRPD pattern and/or DSC profile which is substantially unchanged after storage for 1 month, 2 months, 3 months, 4 months, 5 months, 6 months, 7 months, 8 months, 9 months, 10 months, 1 year, 2 years, 3 years, 4 years, 5 years, 68 months, 6 years, 7 years, 8 years, 9 years, 10 years, 11 years, 140 months, 12 years, 13 years, 14 years, or 15 years at standard warehouse conditions (15° C.-25° C. and ≤65% relative humidity). In some aspects, the crystalline Form IV composition of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 3 months at standard warehouse conditions (15° C.-25° C. and ≤65% relative humidity). In some aspects, the crystalline Form IV composition of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 6 months at standard warehouse conditions (15° C.-25° C. and ≤65% relative humidity). In some aspects, the crystalline Form IV composition of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 1 year at standard warehouse conditions (15° C.-25° C. and ≤65% relative humidity). In some aspects, the crystalline Form IV composition of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 5 years at standard warehouse conditions (15° C.-25° C. and ≤65% relative humidity). In some aspects, the crystalline Form IV composition of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 68 months at standard warehouse conditions (15° C.-25° C. and ≤65% relative humidity). In some aspects, the crystalline Form IV composition of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for ≥140 months at standard warehouse conditions (15° C.-25° C. and ≤65% relative humidity). In some aspects, the crystalline Form IV composition of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for ≥14 years at standard warehouse conditions (15° C.-25° C. and ≤65% relative humidity).

In some aspects, the XRPD pattern for Form IV of N—((R)-2,3-dihydroxypropoxy)-3,4-difluoro-2-(2-fluoro-4-iodo-phenylamino)-benzamide included in the pharmaceutical compositions described herein is generated using a PANALYTICAL® X'Pert Pro diffractometer using Ni-filtered Cu Kα (45 kV/40 mA) radiation and a step size of 0.03° 2θ with a X'CELERATOR® Real Time Multi-Strip detector, configured (a) on the incidental beam side as follows: variable divergence slits (10 mm irradiated length), 0.04 rad Soller slits, fixed anti-scatter slit (0.50°), and 10 mm beam mask, and (b) on the diffracted beam side as follows: variable anti-scatter slit (10 mm observed length) and 0.04 rad Soller slit or a BRUKER® D8® ADVANCE™ system using Cu Kα (40 kV/40 mA) radiation and a step size of 0.03° 2θ with a LYNXEYE™ detector, configured (a) on the incidental beam side as follows: Goebel mirror, mirror exit slit (0.2 mm), 2.5° Soller slit, beam knife, and (b) on the diffracted beam side as follows: anti-scatter slit (8 mm) and 2.5° Soller slit; wherein samples are mounted flat on zero-background Si wafers.

In some aspects, the DSC pattern is generated using a TA Instruments Q100 or Q2000 differential scanning calorimeter at a rate of temperature increase of about 15° C./min. In some aspects, the crystalline form of N—((R)-2,3-dihydroxypropoxy)-3,4-difluoro-2-(2-fluoro-4-iodo-phenylamino)-benzamide included in the pharmaceutical compositions described herein is characterized by an XRPD pattern having peaks at 10.6±0.2, 13.7±0.2, 19.0±0.2, and 23.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having one or more peaks at 10.6±0.2, 13.7±0.2, 14.6±0.2, 17.3±0.2, 18.0±0.2, 18.2±0.2, 19.0±0.2, 19.3±0.2, 20.1±0.2, 21.0±0.2, 21.9±0.2, 22.4±0.2, 23.7±0.2, 24.0±0.2, 24.9±0.2, 26.3±0.2, 27.6±0.2, 28.0±0.2, 30.1±0.2, 32.1±0.2, 32.3±0.2, 32.9±0.2, 35.8±0.2, and 37.7±0.2 degrees two theta.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is characterized by a DSC profile with an endotherm with onset at about 117° C.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is Form I.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is characterized by an XRPD pattern having peaks at 5.5±0.2 and/or 19.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 10.7±0.2, 16.5±0.2, 19.6±0.2, 22.0±0.2, 22.5±0.2, 23.6±0.2, 24.1±0.2, 25.0±0.2, 26.2±0.2, 27.6±0.2, 29.1±0.2, 30.5±0.2, 31.7±0.2, 33.3±0.2, and 39.0±0.2 degrees two theta.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is characterized by a DSC profile with an endotherm with onset at about 87° C.

In some aspects, the crystalline form of N—((R)-2,3-dihydroxypropoxy)-3,4-difluoro-2-(2-fluoro-4-iodo-phenylamino)-benzamide included in the pharmaceutical compositions described herein is Form II.

In some aspects, the present disclosure provides a pharmaceutical composition (e.g., a dispersible tablet, dispersible powder, dispersible granules, dispersible minitablets, or dispersible pellets) comprising N—((R)-2,3-dihydroxypropoxy)-3,4-difluoro-2-(2-fluoro-4-iodo-phenylamino)-benzamide. In some aspects, the pharmaceutical composition (e.g., a dispersible tablet, dispersible powder, dispersible granules, dispersible minitablets, or dispersible pellets) further comprises one or more pharmaceutically acceptable carriers.

In some aspects, the pharmaceutical composition is for oral administration. In some aspects, the pharmaceutical composition is orodispersible.

In some aspects, the potable liquid is water, milk or a juice (e.g., orange juice or apple juice). In some aspects, the potable liquid is water. In some aspects, the potable liquid is a juice.

In some aspects, the pharmaceutical composition is a tablet, a powder, granules, minitablets, or pellets.

In some aspects, the pharmaceutical composition is a powder. In some aspects, the powder is a dispersible powder. In some aspects, a capsule or sachet comprises the dispersible powder.

In some aspects, the pharmaceutical composition is in the form of granules. In some aspects, the granules are dispersible granules. In some aspects, a capsule or sachet comprises the dispersible granules.

In some aspects, the pharmaceutical composition is in the form of minitablets. In some aspects, the minitablets are dispersible minitablets. In some aspects, a capsule or sachet comprises the dispersible minitablets.

In some aspects, the pharmaceutical composition is in the form of pellets. In some aspects, the pellets are dispersible pellets. In some aspects, a capsule or sachet comprises the dispersible pellets.

In some aspects, the pharmaceutical composition is a tablet. In some aspects, the tablet is a dispersible tablet. In some aspects, the dispersible tablet is an orodispersible tablet.

In some aspects, the pharmaceutical composition that is a dispersible tablet, dispersible powder, dispersible granules, dispersible minitablets, or dispersible pellets comprises about 0.1 mg to about 20 mg of N—((R)-2,3-dihydroxypropoxy)-3,4-difluoro-2-(2-fluoro-4-iodo-phenylamino)-benzamide wherein each component of the pharmaceutical composition is as follows: (a) about 0.1 wt/wt % to about 7 wt/wt % of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) about 0 wt/wt % to about 5 wt/wt % of one or more lubricants.

In some aspects, the pharmaceutical composition that is a dispersible tablet, dispersible powder, dispersible granules, dispersible minitablets, or dispersible pellets comprises about 0.1 mg to about 20 mg of N—((R)-2,3-dihydroxypropoxy)-3,4-difluoro-2-(2-fluoro-4-iodo-phenylamino)-benzamide wherein each component of the pharmaceutical composition is as follows: (a) about 0.2 wt/wt % to about 1.5 wt/wt % of N—((R)-2,3-dihydroxypropoxy)-3,4-difluoro-2-(2-fluoro-4-iodo-phenylamino)-benzamide; (b) about 75 wt/wt % to about 98 wt/wt % of one or more diluents; (c) about 3 wt/wt % to about 8 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pharmaceutical composition that is a dispersible tablet, dispersible powder, dispersible granules, dispersible minitablets, or dispersible pellets comprises about 0.1 mg to about 20 mg of N—((R)-2,3-dihydroxypropoxy)-3,4-difluoro-2-(2-fluoro-4-iodo-phenylamino)-benzamide, wherein each component of the pharmaceutical composition is as follows: (a) about 0.5 wt/wt % to about 1.2 wt/wt % of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pharmaceutical composition that is a dispersible tablet, dispersible powder, dispersible granules, dispersible minitablets, or dispersible pellets comprises about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 0.5 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 1 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 2 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 3 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 4 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 5 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 6 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 7 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 8 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 9 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 10 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 11 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 12 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 13 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 14 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 15 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 16 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 17 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 18 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 19 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 20 mg of N—((R)-2,3-dihydroxypropoxy)-3,4-difluoro-2-(2-fluoro-4-iodo-phenylamino)-benzamide.

In some aspects, the pharmaceutical composition that is a dispersible tablet, dispersible powder, dispersible granules, dispersible minitablets, or dispersible pellets comprises about 0.1 wt/wt % to about 7 wt/wt % of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 0.1 wt/wt % to about 5 wt/wt % of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.75 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, about 5 wt/wt %, about 5.1 wt/wt %, about 5.2 wt/wt %, about 5.3 wt/wt %, about 5.4 wt/wt %, about 5.5 wt/wt %, about 5.6 wt/wt %, about 5.7 wt/wt %, about 5.8 wt/wt %, about 5.9 wt/wt %, about 6 wt/wt %, about 6.1 wt/wt %, about 6.2 wt/wt %, about 6.3 wt/wt %, about 6.4 wt/wt %, about 6.5 wt/wt %, about 6.6 wt/wt %, about 6.7 wt/wt %, about 6.8 wt/wt %, about 6.9 wt/wt %, or about 7 wt/wt % of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 0.5 wt/wt % of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 0.8 wt/wt % of N—((R)-2,3-dihydroxypropoxy)-3,4-difluoro-2-(2-fluoro-4-iodo-phenylamino)-benzamide.

In some aspects, the pharmaceutical composition that is a dispersible tablet, dispersible powder, dispersible granules, dispersible minitablets, or dispersible pellets comprises one or more diluents. In some aspects, the pharmaceutical composition that is a dispersible tablet, dispersible powder, dispersible granules, dispersible minitablets, or dispersible pellets comprises about 50 wt/wt % to about 98 wt/wt % of one or more diluents. In some aspects, the pharmaceutical composition that is a dispersible tablet, dispersible powder, dispersible disgranules, dispersible minitablets, or dispersible pellets comprises about 75 wt/wt % to about 98 wt/wt % of one or more diluents. In some aspects, the pharmaceutical composition comprises about 85 wt/wt % to about 95 wt/wt % of one or more diluents. In some aspects, the pharmaceutical composition that is a dispersible tablet, dispersible powder, dispersible granules, dispersible minitablets, or dispersible pellets comprises about 50 wt/wt %, about 51 wt/wt %, about 52 wt/wt %, about 53 wt/wt %, about 54 wt/wt %, about 55 wt/wt %, about 56 wt/wt %, about 57 wt/wt %, about 58 wt/wt %, about 59 wt/wt %, about 60 wt/wt %, about 61 wt/wt %, about 62 wt/wt %, about 63 wt/wt %, about 64 wt/wt %, about 65 wt/wt %, about 66 wt/wt %, about 67 wt/wt %, about 68 wt/wt %, about 69 wt/wt %, about 70 wt/wt %, about 71 wt/wt %, about 72 wt/wt %, about 73 wt/wt %, about 74 wt/wt %, about 75 wt/wt %, about 76 wt/wt %, about 77 wt/wt %, about 78 wt/wt %, about 79 wt/wt %, about 80 wt/wt %, about 81 wt/wt %, about 82 wt/wt %, about 83 wt/wt %, about 84 wt/wt %, about 85 wt/wt %, about 86 wt/wt %, about 87 wt/wt %, about 88 wt/wt %, about 89 wt/wt %, about 90 wt/wt %, about 91 wt/wt %, about 92 wt/wt %, about 93 wt/wt %, about 94 wt/wt %, about 95 wt/wt %, about 96 wt/wt %, about 97 wt/wt %, or about 98 wt/wt % of one or more diluents. In some aspects, the pharmaceutical composition that is a dispersible tablet, dispersible powder, dispersible granules, dispersible minitablets, or dispersible pellets comprises about 90 wt/wt % of one or more diluents. In some aspects, the pharmaceutical composition that is a dispersible tablet, dispersible powder, dispersible granules, dispersible minitablets, or dispersible pellets comprises about 91 wt/wt % of one or more diluents. In some aspects, the pharmaceutical composition that is a dispersible tablet, dispersible powder, dispersible granules, dispersible minitablets, or dispersible pellets comprises about 92 wt/wt % of one or more diluents. In some aspects, the pharmaceutical composition that is a dispersible tablet, dispersible powder, dispersible granules, dispersible minitablets, or dispersible pellets comprises about 93 wt/wt % of one or more diluents.

In some aspects, at least one of the diluents is selected from the group consisting of microcrystalline cellulose, lactose, mannitol, sorbitol, xylitol, sucrose, pregelatinized starch, calcium sulfate, calcium carbonate, starch, and dibasic calcium phosphate. In some aspects, at least one of the diluents is microcrystalline cellulose. In some aspects, the pharmaceutical composition comprises about 50 wt/wt % to about 98 wt/wt % microcrystalline cellulose. In some aspects, the pharmaceutical composition comprises about 75 wt/wt % to about 98 wt/wt % microcrystalline cellulose. In some aspects, the pharmaceutical composition that is a dispersible tablet, dispersible powder, dispersible granules, dispersible minitablets, or dispersible pellets comprises about 85 wt/wt % to about 95 wt/wt % microcrystalline cellulose. In some aspects, the pharmaceutical composition comprises about 50 wt/wt %, about 51 wt/wt %, about 52 wt/wt %, about 53 wt/wt %, about 54 wt/wt %, about 55 wt/wt %, about 56 wt/wt %, about 57 wt/wt %, about 58 wt/wt %, about 59 wt/wt %, about 60 wt/wt %, about 61 wt/wt %, about 62 wt/wt %, about 63 wt/wt %, about 64 wt/wt %, about 65 wt/wt %, about 66 wt/wt %, about 67 wt/wt %, about 68 wt/wt %, about 69 wt/wt %, about 70 wt/wt %, about 71 wt/wt %, about 72 wt/wt %, about 73 wt/wt %, about 74 wt/wt %, about 75 wt/wt %, about 76 wt/wt %, about 77 wt/wt %, about 78 wt/wt %, about 79 wt/wt %, about 80 wt/wt %, about 81 wt/wt %, about 82 wt/wt %, about 83 wt/wt %, about 84 wt/wt %, about 85 wt/wt %, about 86 wt/wt %, about 87 wt/wt %, about 88 wt/wt %, about 89 wt/wt %, about 90 wt/wt %, about 91 wt/wt %, about 92 wt/wt %, about 93 wt/wt %, about 94 wt/wt %, about 95 wt/wt, about 96 wt/wt %, about 97 wt/wt %, or about 98 wt/wt % microcrystalline cellulose. In some aspects, the pharmaceutical composition that is a dispersible tablet, dispersible powder, dispersible granules, dispersible minitablets, or dispersible pellets comprises about 90 wt/wt % microcrystalline cellulose. In some aspects, the pharmaceutical composition that is a dispersible tablet, dispersible powder, dispersible granules, dispersible minitablets, or dispersible pellets comprises about 91 wt/wt % microcrystalline cellulose. In some aspects, the pharmaceutical composition that is a dispersible tablet, dispersible powder, dispersible granules, dispersible minitablets, or dispersible pellets comprises about 92 wt/wt % microcrystalline cellulose. In some aspects, the pharmaceutical composition that is a dispersible tablet, dispersible powder, dispersible granules, dispersible minitablets, or dispersible pellets comprises about 93 wt/wt % microcrystalline cellulose.

In some aspects, the pharmaceutical composition that is a dispersible tablet, dispersible powder, dispersible granules, dispersible minitablets, or dispersible pellets comprises about 1.0 wt/wt % to about 10 wt/wt % of one or more disintegrants. In some aspects, the pharmaceutical composition that is a dispersible tablet, dispersible powder, dispersible granules, dispersible minitablets, or dispersible pellets comprises about 3.5 wt/wt % to about 6 wt/wt % of one or more disintegrants. In some aspects, the pharmaceutical composition comprises about 1.0 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2.0 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, about 5.0 wt/wt %, about 5.1 wt/wt %, about 5.2 wt/wt %, about 5.3 wt/wt %, about 5.4 wt/wt %, about 5.5 wt/wt %, about 5.6 wt/wt %, about 5.7 wt/wt %, about 5.8 wt/wt %, about 5.9 wt/wt %, about 6.0 wt/wt %, about 6.1 wt/wt %, about 6.2 wt/wt %, about 6.3 wt/wt %, about 6.4 wt/wt %, about 6.5 wt/wt %, about 6.6 wt/wt %, about 6.7 wt/wt %, about 6.8 wt/wt %, about 6.9 wt/wt %, about 7.0 wt/wt %, about 7.1 wt/wt %, about 7.2 wt/wt %, about 7.3 wt/wt %, about 7.4 wt/wt %, about 7.5 wt/wt %, about 7.6 wt/wt %, about 7.7 wt/wt %, about 7.8 wt/wt %, about 7.9 wt/wt %, about 8.0 wt/wt %, about 8.1 wt/wt %, about 8.2 wt/wt %, about 8.3 wt/wt %, about 8.4 wt/wt %, about 8.5 wt/wt %, about 8.6 wt/wt %, about 8.7 wt/wt %, about 8.8 wt/wt %, about 8.9 wt/wt %, about 9.0 wt/wt %, about 9.1 wt/wt %, about 9.2 wt/wt %, about 9.3 wt/wt %, about 9.4 wt/wt %, about 9.5 wt/wt %, about 9.6 wt/wt %, about 9.7 wt/wt %, about 9.8 wt/wt %, about 9.9 wt/wt %, or about 10.0 wt/wt % of one or more disintegrants. In some aspects, the pharmaceutical composition that is a dispersible tablet, dispersible powder, dispersible granules, dispersible minitablets, or dispersible pellets comprises about 5 wt/wt % of one or more disintegrants.

In some aspects, at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid. In some aspects, at least one of the disintegrants is croscarmellose sodium. In some aspects, the disintegrant is croscarmellose sodium. In some aspects, the pharmaceutical composition that is a dispersible tablet, dispersible powder, dispersible granules, dispersible minitablets, or dispersible pellets comprises about 1.0 wt/wt % to about 10 wt/wt % croscarmellose sodium. In some aspects, the pharmaceutical composition that is a dispersible tablet, dispersible powder, dispersible granules, dispersible minitablets, or dispersible pellets comprises about 3.5 wt/wt % to about 6 wt/wt % croscarmellose sodium. In some aspects, the pharmaceutical composition comprises about about 1.0 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2.0 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, 3.5 wt/wt % about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, about 5 wt/wt %, about 5.1 wt/wt %, about 5.2 wt/wt %, about 5.3 wt/wt %, about 5.4 wt/wt %, about 5.5 wt/wt %, about 5.6 wt/wt %, about 5.7 wt/wt %, about 5.8 wt/wt %, about 5.9 wt/wt %, about 6.0 wt/wt %, about 6.1 wt/wt %, about 6.2 wt/wt %, about 6.3 wt/wt %, about 6.4 wt/wt %, about 6.5 wt/wt %, about 6.6 wt/wt %, about 6.7 wt/wt %, about 6.8 wt/wt %, about 6.9 wt/wt %, about 7.0 wt/wt %, about 7.1 wt/wt %, about 7.2 wt/wt %, about 7.3 wt/wt %, about 7.4 wt/wt %, about 7.5 wt/wt %, about 7.6 wt/wt %, about 7.7 wt/wt %, about 7.8 wt/wt %, about 7.9 wt/wt %, about 8.0 wt/wt %, about 8.1 wt/wt %, about 8.2 wt/wt %, about 8.3 wt/wt %, about 8.4 wt/wt %, about 8.5 wt/wt %, about 8.6 wt/wt %, about 8.7 wt/wt %, about 8.8 wt/wt %, about 8.9 wt/wt %, about 9.0 wt/wt %, about 9.1 wt/wt %, about 9.2 wt/wt %, about 9.3 wt/wt %, about 9.4 wt/wt %, about 9.5 wt/wt %, about 9.6 wt/wt %, about 9.7 wt/wt %, about 9.8 wt/wt %, about 9.9 wt/wt %, or about 10.0 wt/wt % croscarmellose sodium. In some aspects, the pharmaceutical composition that is a dispersible tablet, dispersible powder, dispersible granules, dispersible minitablets, or dispersible pellets comprises about 5 wt/wt % croscarmellose sodium.

In some aspects, the pharmaceutical composition that is a dispersible tablet, dispersible powder, dispersible granules, dispersible minitablets, or dispersible pellets comprises 0 wt/wt % to about 5 wt/wt % of one or more flavoring agents. In some aspects, the pharmaceutical composition that is a dispersible tablet, dispersible powder, dispersible granules, dispersible minitablets, or dispersible pellets comprises 0 wt/wt % to about 2.5 wt/wt % of one or more flavoring agents. In some aspects, the pharmaceutical composition that is a dispersible tablet, dispersible powder, dispersible granules, dispersible minitablets, or dispersible pellets comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5.0 wt/wt % of one or more flavoring agents. In some aspects, the pharmaceutical composition that is a dispersible tablet, dispersible powder, dispersible granules, dispersible minitablets, or dispersible pellets comprises about 2 wt/wt % of one or more flavoring agents.

In some aspects, at least one of the flavoring agents is selected from the group consisting of natural or synthetic flavors including but not limited to, grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring. In some aspects, at least one of the flavoring agents is grape flavoring. In some aspects, the pharmaceutical composition that is a dispersible tablet, dispersible powder, dispersible granules, dispersible minitablets, or dispersible pellets comprises 0 wt/wt % to about 5.0 wt/wt % grape flavoring. In some aspects, the pharmaceutical composition that is a dispersible tablet, dispersible powder, dispersible granules, dispersible minitablets, or dispersible pellets comprises 0 wt/wt % to about 2.5 wt/wt % grape flavoring. In some aspects, the pharmaceutical composition that is a dispersible tablet, dispersible powder, dispersible granules, dispersible minitablets, or dispersible pellets comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about or about 5.0 wt/wt % grape flavoring. In some aspects, the pharmaceutical composition that is a dispersible tablet, dispersible powder, dispersible granules, dispersible minitablets, or dispersible pellets comprises about 2 wt/wt % grape flavoring.

In some aspects, the pharmaceutical composition that is a dispersible tablet, dispersible powder, dispersible granules, dispersible minitablets, or dispersible pellets comprises 0 wt/wt % to about 5 wt/wt % of one or more sweeteners. In some aspects, the pharmaceutical composition that is a dispersible tablet, dispersible powder, dispersible granules, dispersible minitablets, or dispersible pellets comprises 0 wt/wt % to about 2 wt/wt % of one or more sweeteners. In some aspects, the pharmaceutical composition that is a dispersible tablet, dispersible powder, dispersible granules, dispersible minitablets, or dispersible pellets comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5.0 wt/wt % of one or more sweeteners. In some aspects, the pharmaceutical composition that is a dispersible tablet, dispersible powder, dispersible granules, dispersible minitablets, or dispersible pellets comprises about 1 wt/wt % of one or more sweeteners.

In some aspects, at least one of the sweeteners is selected from the group consisting of sucralose, acesulfame, saccharin, sucrose, xylitol, mannitol, sorbitol, glucose, fructose, and aspartame. In some aspects, at least one of the sweeteners is sucralose. In some aspects, the sweetener is sucralose. In some aspects, the pharmaceutical composition that is a dispersible tablet, dispersible powder, dispersible granules, dispersible minitablets, or dispersible pellets comprises 0 wt/wt % to about 5 wt/wt % sucralose. In some aspects, the pharmaceutical composition that is a dispersible tablet, dispersible powder, dispersible granules, dispersible minitablets, or dispersible pellets comprises 0 wt/wt % to about 2 wt/wt % sucralose. In some aspects, the pharmaceutical composition that is a dispersible tablet, dispersible powder, dispersible granules, dispersible minitablets, or dispersible pellets comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5 wt/wt % sucralose. In some aspects, the pharmaceutical composition that is a dispersible tablet, dispersible powder, dispersible granules, dispersible minitablets, or dispersible pellets comprises about 1 wt/wt % sucralose.

In some aspects, the pharmaceutical composition that is a dispersible tablet, dispersible powder, dispersible granules, dispersible minitablets, or dispersible pellets comprises 0 wt/wt % to about 5 wt/wt % of one or more lubricants. In some aspects, the pharmaceutical composition that is a dispersible tablet, dispersible powder, dispersible granules, dispersible minitablets, or dispersible pellets comprises about 0.1 wt/wt % to about 5 wt/wt % of one or more lubricants. In some aspects, the pharmaceutical composition that is a dispersible tablet, dispersible powder, dispersible granules, dispersible minitablets, or dispersible pellets comprises about 0.5 wt/wt % to about 2 wt/wt % of one or more lubricants. In some aspects, the pharmaceutical composition comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5 wt/wt % of one or more lubricants. In some aspects, the pharmaceutical composition that is a dispersible tablet, dispersible powder, dispersible granules, dispersible minitablets, or dispersible pellets comprises about 1 wt/wt % of one or more lubricants.

In some aspects, at least one of the lubricants is selected from the group consisting of magnesium stearate, sodium stearyl fumarate, glycerol dibehenate, stearic acid, hydrogenated vegetable oil, calcium stearate, zinc stearate, beeswax, colloidal silicon dioxide, and talc. In some aspects, at least one of the lubricants is magnesium stearate. In some aspects, the pharmaceutical composition that is a dispersible tablet, dispersible powder, dispersible granules, dispersible minitablets, or dispersible pellets comprises 0 wt/wt % to about 5 wt/wt % magnesium stearate. In some aspects, the pharmaceutical composition that is a dispersible tablet, dispersible powder, dispersible granules, dispersible minitablets, or dispersible pellets comprises about 0.1 wt/wt % to about 2 wt/wt % magnesium stearate. In some aspects, the pharmaceutical composition that is a dispersible tablet, dispersible powder, dispersible granules, dispersible minitablets, or dispersible pellets comprises about 0.5 wt/wt % to about 2 wt/wt % magnesium stearate. In some aspects, the pharmaceutical composition that is a dispersible tablet, dispersible powder, dispersible granules, dispersible minitablets, or dispersible pellets comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about or about 5 wt/wt % magnesium stearate. In some aspects, the pharmaceutical composition that is a dispersible tablet, dispersible powder, dispersible granules, dispersible minitablets, or dispersible pellets comprises 0 wt/wt % magnesium stearate. In some aspects, the pharmaceutical composition that is a dispersible tablet, dispersible powder, dispersible granules, dispersible minitablets, or dispersible pellets comprises about 1 wt/wt % magnesium stearate.

Methods of Treatment and Uses

In some aspects, the present disclosure provides a method of treating a tumor, a cancer, or a Rasopathy disorder comprising administering to a subject in need of such treatment a pharmaceutical composition described herein.

In some aspects, the tumor is a neurofibroma. In some aspects, the tumor is a neurofibroma associated with Neurofibromatosis Type 1. In some aspects, the tumor is selected from the group consisting of cutaneous neurofibroma, plexiform neurofibroma, optic pathway glioma, low grade glioma, high grade glioma, or malignant peripheral nerve sheath tumor. In some aspects, the tumor is plexiform neurofibroma.

In some aspects, the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

In some aspects, the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum. In some aspects, the leukemia is selected from the group consisting of acute lymphocytic leukemia, acute myelogenous leukemia, chronic lymphocytic leukemia, and chronic myelogenous leukemia. In some aspects, the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia. In some aspects, the lung cancer is selected from the group consisting of lung adenocarcinoma, squamous non-small cell lung cancer, non-squamous non-small cell lung cancer, and small cell lung cancer.

In some aspects, the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

In some aspects, an individual dose of the N—((R)-2,3-dihydroxypropoxy)-3,4-difluoro-2-(2-fluoro-4-iodo-phenylamino)-benzamide is administered as more than one tablet, more than one dose of dispersible powder, more than one dose of dispersible granules, more than one dose of minitablets, more than one dose of pellets, or a combination thereof. For example, a dose of 3 mg of the N—((R)-2,3-dihydroxypropoxy)-3,4-difluoro-2-(2-fluoro-4-iodo-phenylamino)-benzamide can be administered as two dispersible tablets—one containing 2 mg and the other containing 1 mg or as three dispersible tablets each containing 1 mg.

In some aspects, the N—((R)-2,3-dihydroxypropoxy)-3,4-difluoro-2-(2-fluoro-4-iodo-phenylamino)-benzamide is provided in an amount of about 0.1 mg to about 20 mg per dose of the pharmaceutical compositions described herein. In some aspects, the N—((R)-2,3-dihydroxypropoxy)-3,4-difluoro-2-(2-fluoro-4-iodo-phenylamino)-benzamide is provided in an amount of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg per dose. In some aspects, the N—((R)-2,3-dihydroxypropoxy)-3,4-difluoro-2-(2-fluoro-4-iodo-phenylamino)-benzamide is provided in an amount of about 0.5 mg per dose. In some aspects, the N—((R)-2,3-dihydroxypropoxy)-3,4-difluoro-2-(2-fluoro-4-iodo-phenylamino)-benzamide is provided in an amount of about 1 mg per dose. In some aspects, the N—((R)-2,3-dihydroxypropoxy)-3,4-difluoro-2-(2-fluoro-4-iodo-phenylamino)-benzamide is provided in an amount of about 2 mg per dose. In some aspects, the N—((R)-2,3-dihydroxypropoxy)-3,4-difluoro-2-(2-fluoro-4-iodo-phenylamino)-benzamide is provided in an amount of about 3 mg per dose. In some aspects, the N—((R)-2,3-dihydroxypropoxy)-3,4-difluoro-2-(2-fluoro-4-iodo-phenylamino)-benzamide is provided in an amount of about 4 mg per dose. In some aspects, the N—((R)-2,3-dihydroxypropoxy)-3,4-difluoro-2-(2-fluoro-4-iodo-phenylamino)-benzamide is provided in an amount of about 5 mg per dose. In some aspects, the N—((R)-2,3-dihydroxypropoxy)-3,4-difluoro-2-(2-fluoro-4-iodo-phenylamino)-benzamide is provided in an amount of about 10 mg per dose. In some aspects, the N—((R)-2,3-dihydroxypropoxy)-3,4-difluoro-2-(2-fluoro-4-iodo-phenylamino)-benzamide is provided in an amount of about 20 mg per dose.

In some aspects, the pharmaceutical composition comprising N—((R)-2,3-dihydroxypropoxy)-3,4-difluoro-2-(2-fluoro-4-iodo-phenylamino)-benzamide is administered one time, two times, three times, or four times per day. In some aspects, the total daily dose of the N—((R)-2,3-dihydroxypropoxy)-3,4-difluoro-2-(2-fluoro-4-iodo-phenylamino)-benzamide is administered two times per day.

In some aspects, the N—((R)-2,3-dihydroxypropoxy)-3,4-difluoro-2-(2-fluoro-4-iodo-phenylamino)-benzamide is administered in a total daily dose that does not exceed 1 mg, 2 mg, 3 mg, 4 mg, 5 mg, 6 mg, 7 mg, 8 mg, 9 mg, or 10 mg. In some aspects, the N—((R)-2,3-dihydroxypropoxy)-3,4-difluoro-2-(2-fluoro-4-iodo-phenylamino)-benzamide is administered in a total daily dose that does not exceed 8 mg. In some aspects, the N—((R)-2,3-dihydroxypropoxy)-3,4-difluoro-2-(2-fluoro-4-iodo-phenylamino)-benzamide is administered in a total daily dose does not exceed 2 mg. In some aspects, the N—((R)-2,3-dihydroxypropoxy)-3,4-difluoro-2-(2-fluoro-4-iodo-phenylamino)-benzamide is administered in a total daily dose that does not exceed 1 mg.

In some aspects, the N—((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising (a) 21 consecutive days in which the total daily dose is administered; followed by (b) 7 consecutive days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising (a) three 7-day periods each comprising (i) 5 days in which the total daily dose is administered and (ii) 2 days in which no N—((R)-2,3-dihydroxypropoxy)-3,4-difluoro-2-(2-fluoro-4-iodo-phenylamino)-benzamide; and (b) 7 days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising (a) three 7-day periods each comprising (i) 5 consecutive days in which the total daily dose is administered and (ii) 2 consecutive days in which no N—((R)-2,3-dihydroxypropoxy)-3,4-difluoro-2-(2-fluoro-4-iodo-phenylamino)-benzamide; followed by (b) 7 consecutive days in which no N—((R)-2,3-dihydroxypropoxy)-3,4-difluoro-2-(2-fluoro-4-iodo-phenylamino)-benzamide is administered.

In some aspects, the N—((R)-2,3-dihydroxypropoxy)-3,4-difluoro-2-(2-fluoro-4-iodo-phenylamino)-benzamide is administered on a 28-day dosing cycle comprising 28 days in which the total daily dose is administered.

In some aspects, the 28-day dosing cycle is repeated up to a total of 24 consecutive 28-day dosing cycles.

In some aspects, the subject experiences dysphagia. In some aspects, the subject experiences dysphagia caused by one or more of: disease of the nervous system, muscle weakening, developmental disability, stroke, injury, anatomical defect, cancer, treatment for cancer, allergic reaction, dementia, memory loss, or cognitive decline. In some aspects, the subject has been diagnosed with an autism spectrum disorder. In some aspects, the subject has been diagnosed with a craniofacial disorder. In some aspects, the subject has been diagnosed with myasthenia gravis. In some aspects, the subject has been diagnosed with tardive dyskinesia.

In some aspects, the subject is a pediatric subject. In some aspects, the subject is less than 18 years old, less than 17 years old, less than 16 years old, less than 15 years old, less than 14 years old, less than 13 years old, less than 12 years old, less than 11 years old, less than 10 years old, less than 9 years old, less than 8 years old, less than 7 years old, less than 6 years old, less than 5 years old, less than 4 years old, less than 3 years old, less than 2 years old, or less than 1 year old. In some aspects, the subject is 1 year old, 2 years old, 3 years old, 4 years old, 5 years old, 6 years old, 7 years old, 8 years old, 9 years old, 10 years old, 11 years old, 12 years old, 13 years old, 14 years old, 15 years old, 16 years old, or 17 years old. In some aspects, the subject is less than 13 years old. In some aspects, the subject is less than 12 years old. In some aspects, the subject is less than 11 years old. In some aspects, the subject is less than 10 years old. In some aspects, the subject is less than 9 years old. In some aspects, the subject is less than 8 years old. In some aspects, the subject is less than 7 years old. In some aspects, the subject is less than 6 years old. In some aspects, the subject is less than 5 years old. In some aspects, the subject is less than 4 years old. In some aspects, the subject is less than 3 years old. In some aspects, the subject is less than 2 years old. In some aspects, the subject is less than 1 year old. In some aspects, the subject is about 2 to about 18 years old. In some aspects, the subject is about 3 to about 17 years old. In some aspects, the subject is about 4 to about 16 years old. In some aspects, the subject is about 5 to about 15 years old. In some aspects, the subject is about 6 to about 14 years old. In some aspects, the subject is about 7 to about 13 years old. In some aspects, the subject is about 8 to about 12 years old.

In some aspects, the subject is a geriatric subject. In some aspects, the subject is more than 30 years old, more than 35 years old, more than 40 years old, more than 45 years old, more than 50 years old, more than 55 years old, more than 60 years old, more than 65 years old, more than 70 years old, more than 75 years old, more than 80 years old, more than 85 years old, more than 90 years old, more than 95 years old, or more than 100 year old. In some aspects, the subject is more than 50 years old. In some aspects, the subject is more than 60 years old. In some aspects, the subject is more than 70 years old. In some aspects, the subject is more than 80 years old. In some aspects, the subject is more than 90 years old. In some aspects, the subject is more than 100 years old.

In some aspects, if the N—((R)-2,3-dihydroxypropoxy)-3,4-difluoro-2-(2-fluoro-4-iodo-phenylamino)-benzamide is to be administered more than one time a day, the total daily dose of the N—((R)-2,3-dihydroxypropoxy)-3,4-difluoro-2-(2-fluoro-4-iodo-phenylamino)-benzamide can be divided so the patient receives different doses at each administration. For example, if the total daily dose of the N—((R)-2,3-dihydroxypropoxy)-3,4-difluoro-2-(2-fluoro-4-iodo-phenylamino)-benzamide is to be 2 mg administered two times per day, the patient can receive 0.5 mg (e.g., as one 0.5 mg dispersible tablet) in the morning and 1.5 mg (e.g., as one 0.5 mg dispersible tablet and one 1 mg dispersible tablet) in the evening.

In some aspects, the total daily dose of N—((R)-2,3-dihydroxypropoxy)-3,4-difluoro-2-(2-fluoro-4-iodo-phenylamino)-benzamide is administered two times daily. In some aspects, the total daily dose of the N—((R)-2,3- dihydroxypropoxy)-3,4-difluoro-2-(2-fluoro-4-iodo-phenylamino)-benzamide is administered two times daily at a dose of about 0.1 mg to about 10 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, or about 10 mg. In some aspects, the total daily dose of the N—((R)-2,3-dihydroxypropoxy)-3,4-difluoro-2-(2-fluoro-4-iodo-phenylamino)-benzamide is administered two times daily at a dose of about 0.25 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 0.5 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 1 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 2 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 4 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 5 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 10 mg each.

In some aspects, the total daily dose of the N—((R)-2,3-dihydroxypropoxy)-3,4-difluoro-2-(2-fluoro-4-iodo-phenylamino)-benzamide is administered once daily. In some aspects, the total daily dose of the N—((R)-2,3-dihydroxypropoxy)-3,4-difluoro-2-(2-fluoro-4-iodo-phenylamino)-benzamide is administered once daily at a dose of about 0.1 mg to about 20 mg. In some aspects, the total daily dose of the N—((R)-2,3-dihydroxypropoxy)-3,4-difluoro-2-(2-fluoro-4-iodo-phenylamino)-benzamide is administered once daily at a dose of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg. In some aspects, the total daily dose of the N—((R)-2,3-dihydroxypropoxy)-3,4-difluoro-2-(2-fluoro-4-iodo-phenylamino)-benzamide is administered once daily at a dose of about 0.5 mg. In some aspects, the total daily dose of the N—((R)-2,3-dihydroxypropoxy)-3,4-difluoro-2-(2-fluoro-4-iodo-phenylamino)-benzamide is administered once daily at a dose of about 1 mg. In some aspects, the total daily dose of the N—((R)-2,3-dihydroxypropoxy)-3,4-difluoro-2-(2-fluoro-4-iodo-phenylamino)-benzamide is administered once daily at a dose of about 2 mg. In some aspects, the total daily dose of the N—((R)-2,3-dihydroxypropoxy)-3,4-difluoro-2-(2-fluoro-4-iodo-phenylamino)-benzamide is administered once daily at a dose of about 4 mg. In some aspects, the total daily dose of the N—((R)-2,3-dihydroxypropoxy)-3,4-difluoro-2-(2-fluoro-4-iodo-phenylamino)-benzamide is administered once daily at a dose of about 8 mg. In some aspects, the total daily dose of the N—((R)-2,3-dihydroxypropoxy)-3,4-difluoro-2-(2-fluoro-4-iodo-phenylamino)-benzamide is administered once daily at a dose of about 10 mg. In some aspects, the total daily dose of the N—((R)-2,3-dihydroxypropoxy)-3,4-difluoro-2-(2-fluoro-4-iodo-phenylamino)-benzamide is administered once daily at a dose of about 20 mg.

In some aspects, the N—((R)-2,3-dihydroxypropoxy)-3,4-difluoro-2-(2-fluoro-4-iodo-phenylamino)-benzamide is administered via a pharmaceutical composition described herein, wherein the N—((R)-2,3-dihydroxypropoxy)-3,4-difluoro-2-(2-fluoro-4-iodo-phenylamino)-benzamide is provided at a total daily dose that does not exceed 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg. In some aspects, the N—((R)-2,3-dihydroxypropoxy)-3,4-difluoro-2-(2-fluoro-4-iodo-phenylamino)-benzamide is administered in a total daily dose that does not exceed 20 mg. In some aspects, the N—((R)-2,3-dihydroxypropoxy)-3,4-difluoro-2-(2-fluoro-4-iodo-phenylamino)-benzamide is administered in a total daily dose that does not exceed 10 mg. In some aspects, the N—((R)-2,3-dihydroxypropoxy)-3,4-difluoro-2-(2-fluoro-4-iodo-phenylamino)-benzamide is administered in a total daily dose that does not exceed 8 mg. In some aspects, the N—((R)-2,3-dihydroxypropoxy)-3,4-difluoro-2-(2-fluoro-4-iodo-phenylamino)-benzamide is administered in a total daily dose that does not exceed 6 mg. In some aspects, the N—((R)-2,3-dihydroxypropoxy)-3,4-difluoro-2-(2-fluoro-4-iodo-phenylamino)-benzamide is administered in a total daily dose that does not exceed 4 mg. In some aspects, the N—((R)-2,3-dihydroxypropoxy)-3,4-difluoro-2-(2-fluoro-4-iodo-phenylamino)-benzamide is administered in a total daily dose that does not exceed 2 mg. In some aspects, the N—((R)-2,3-dihydroxypropoxy)-3,4-difluoro-2-(2-fluoro-4-iodo-phenylamino)-benzamide is administered in a total daily dose that does not exceed 1 mg.

In some aspects, the present disclosure provides use of a pharmaceutical composition described herein for the manufacture of a medicament for treating a tumor, a cancer, or a Rasopathy disorder.

EXAMPLES

Example 1: Production of Seed Crystals of Form IV

Step 1: Preparation of "Side Chain", PD-0337792

14.4 kg alcohol (chemical purity 99.4%, optical purity 99.6% enantiomeric excess) was converted to 97.5 kg 9.7% w/w PD-0337792 (IPGA) solution in toluene (overall yield ~60%). The triflate activation was performed in the 200 L reactor by maintaining temperatures under −20° C. during triflic anhydride addition. The resulting activated alcohol was then transferred to a 400 L reactor containing solid N-hydroxypthalimide (NHP) and the reaction was allowed to occur at ambient temperature to completion. The final base de-protection was performed by adding aqueous ammonia (~28% soln, 5 equiv., 34 kg). After reaction completion, water was removed by distillation from toluene, and the resulting solid side product was filtered out to yield the product solution.

Step 2: Preparation of PD-0315209

The process yielded 21.4 kg (99.4% w/w assay), which is 80% of theoretical from starting materials 2,3,4-trifluorobenzoic acid (12 kg, 1 eq.) and 2-fluoro-4-iodoaniline (16.4 kg, 1.02 eq.) with lithium amide base (5 kg, 3.2 eq.). The reaction was initiated by adding 5% of total solution of TFBA and FIA into lithium amide slurry at 50° C. This reaction demonstrated a minimal initiation period of ~10 minutes, which was observed by color change and slight exotherm. The remaining TFBA/FIA solution in THF was slowly added through a pressure can in an hour while maintaining the reaction temperatures within 45-55° C. There was no appreciable pressure rise (due to ammonia gas release) observed during the entire operation.

Step 3: Preparation of PD-0325901

A modification was made to the CDI charging to mitigate potential gas generation. Two equal portions of CDI were added into solid FIPFA before and after solvent addition (through a shot loader). The timing between the two solid CDI additions (4.6 kg each) should not exceed 30 minutes. Then two intermediate filter cakes were dissolved with ethanol. The excess ethanol was distilled and replaced with toluene to approximately 5% v/v ethanol prior to PD-0325901 recrystallization. Lab studies suggested that the crystallization from toluene and acetonitrile and recrystallization from ethanol in toluene would not be able to reduce impurities which is essential for the polymorph transformation. The presence of a dimeric impurity (PF-00191189) at a level greater than 0.2% has been known to result in the formation of undesired polymorph.

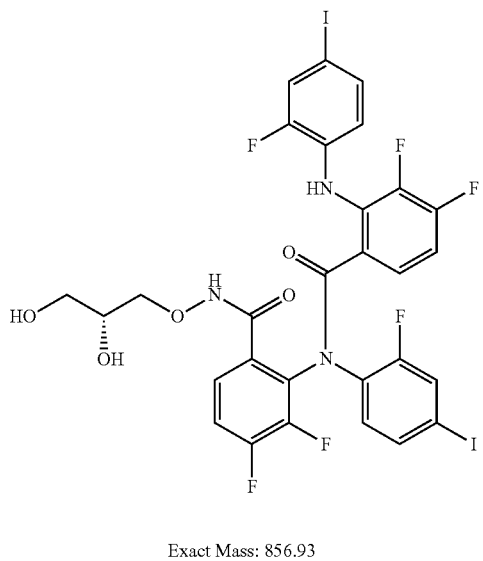

PF-00191189

Exact Mass: 856.93

The crude crystallization from the final reaction mixture reduced dimeric impurity PF-00191189 to approximately 1.9% and the subsequent recrystallization further reduced it to approximately 0.4%. As a consequence, undesired polymorphs were produced. The DSC patterns indicated two different melting points ~80° C. (low melt Form II) and ~117° C. (Form I). Also during the processing, the solids crystallized at a much lower temperature than expected (actual ~10° C., expected ~40° C.). It is suspected that the unsuccessful recrystallization is due to a change in the solvent composition as a result of incomplete drying of the crude. Drying of the crude wet cake prior to ethanol dissolution was stopped after about 36 hours when the crude product was ~28 kg (26 kg theoretical).

Polymorph Transformation

Approximately 7.4 kg of PD-0325901 (mixed polymorphs) from the final EtOH/Water crystallization and precipitated materials from the earlier EtOH/Toluene filtrate were taken forward to the polymorph transformation. Both crops were separately dried in the filter until constant weights and each was dissolved in EtOH. The combined EtOH solution was analyzed by HPLC and resulted in an estimated amount of 16.4 kg PD-0325901. The recrystallization was started after removing EtOH via vacuum distillation and adjusting the solvent composition to about 5% EtOH in Toluene at 65° C. (i.e., EtOH is added dropwise at 65° C. until complete solids dissolution).

A slow 4-hour cooling ramp to 5° C. followed by 12 h stirring was performed to ensure satisfactory results. The resulting slurry was filtered and again it was completely dried in the filter until constant weight (approximately 3 days). The purified solid showed 99.8% pure PD-0325901 with not detected level of dimeric impurity PF-00191189.

The dried solid (15.4 kg) was re-dissolved in exactly 4 volumes of EtOH (62 L) off of the filter, transferred to the reactor and precipitated by a slow (~3 h) water addition (308 L) at 30-35° C., cooled to 20° C. and stirred for 12 h. The DSC analysis of a slurry sample taken at 2 h shows the solids to be completely Form IV (desired polymorph).

21.4 kg PD-0315209, 9.7 kg CDI (1.05 equiv.), 91 kg solution of 9.7% PD-0337792 in Toluene (1.1 equiv.) were used and resulted in 12.74 kg of PD-0325901 (assay 99.4%, 100% Form IV, Yield ~ 48%).

Example 2: Assay/Impurities and Identification of PD-0325901

PD-0325901 is separated from process impurities and degradants by reversed-phase liquid chromatography with UV detection at 275 nm. Identification of PD-0325901 is performed by obtaining either an infrared or proton NMR spectrum, in addition to the HPLC retention time. For purity evaluation, process impurities and degradants are identified by their characteristic relative retention times and quantitated by area normalization.

Chromatographic Conditions: Agilent Zorbax SB C18, 5 μm, 4.6×250 mm (or equivalent); flow rate is 1.0 mL/min; column temperature is 30° C.; detector wavelength is 275 nm; diluent is 50/50 acetonitrile/water; mobile phase A is 0.1% trifluoroacetic acid (TFA) in water; mobile phase B is methanol; and the gradient conditions below. The assay is determined against a reference standard and reported on an anhydrous, solvent free basis. Quantification of specified and unspecified impurities is reported by area percent. Total impurities is the sum of all impurities present above the reporting threshold of 0.05%.

|  | Time (minutes) | | | | |
| --- | --- | --- | --- | --- | --- |
|  | 0 | 15 | 40 | 45 | 46 |
| % mobile phase B | 70 | 70 | 100 | 100 | 70 |

Example 3: Improved Process for Preparation of Form IV

As described in Example 1, synthetic methods of producing mirdametinib as Form IV produced Form IV with dimeric impurity PF-00191189, and further steps were required to transform the product into essentially pure Form IV without undesired polymorphs Form I and Form II.

Therefore, it was necessary to develop a method of producing essentially pure Form IV without additional processing steps.

Mirdametinib Manufacturing Process

The route is a convergent four step synthesis with six chemical steps overall, using the proposed starting materials (S)—(+)-2,2-dimethyl-1,3-dioxolane-4-methanol (SGA), 2,3,4-trifluorobenzoic acid (TFBA), 2-fluoro-4-idodoaniline (FIA), and N-hydroxyphthalimide (NHP). The final step (Step 4) provides essentially pure Form IV of mirdametinib.

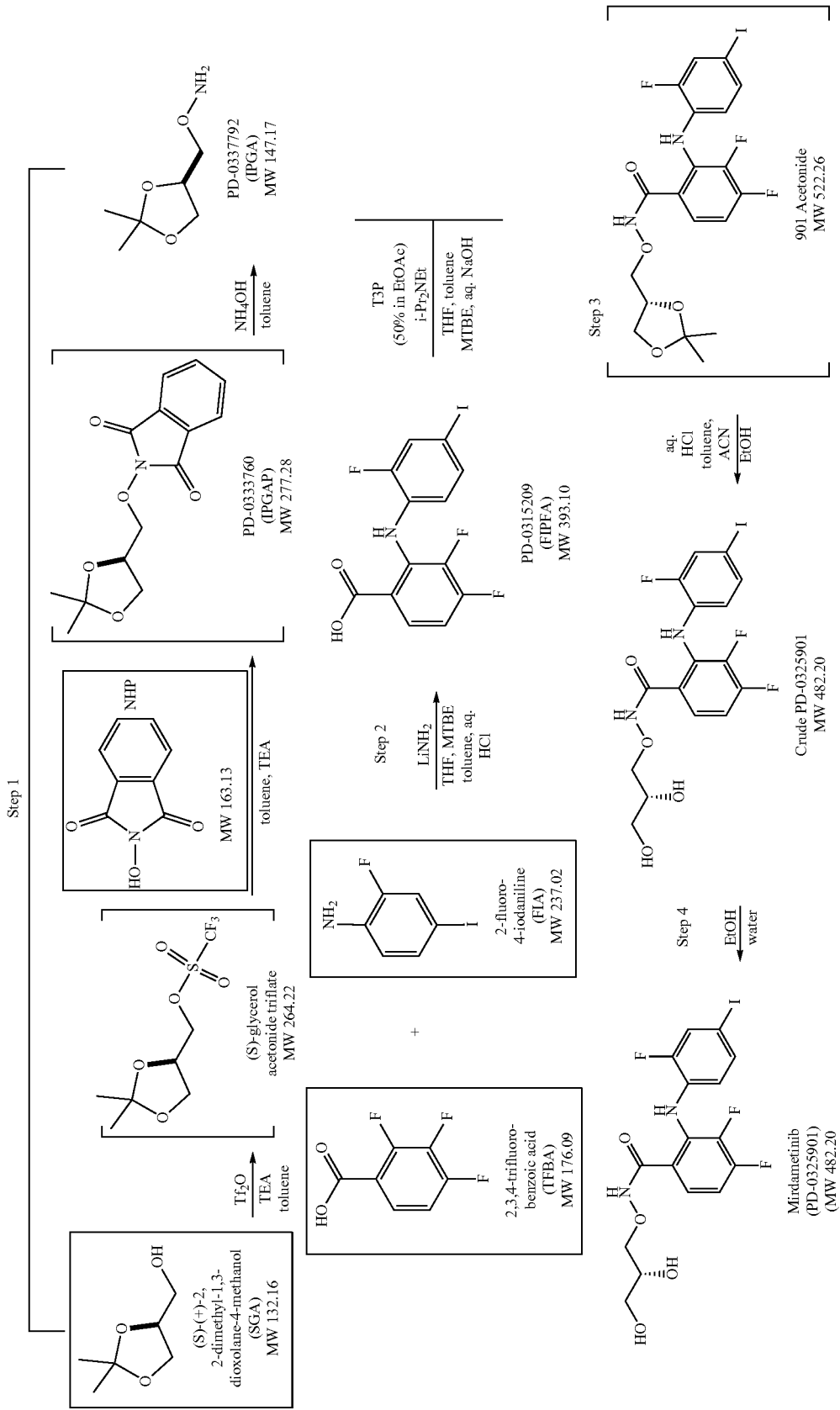

Step 1 (Preparation of PD-0337792 (IPGA)): A clean, dry 100-gallon reactor was charged with toluene (139.3 kg, 8 volumes) and (S)—(+)-2,2-Dimethyl-1,3-dioxolane-4-methanol (SGA; 20.0 kg, 1.0 equivalents). Triethylamine (18.8 kg, 1.22 equivalents) was charged to the reactor. The reactor contents were agitated and cooled to −10±10° C. Trifluoromethanesulfonic anhydride (43.5 kg, 1.02 equivalents) was added to a clean 50-L round bottom flask under nitrogen then cooled to a temperature of ≤−10° C. The cooled trifluoromethanesulfonic anhydride was slowly transferred to the 100-gallon reactor while maintaining the internal temperature at −10±10° C. The reaction mixture was agitated at −10±10° C. for 30 minutes. Reaction monitoring by TLC indicated the conversion to be complete. While maintaining the internal temperature at −10±10° C., anhydrous toluene (99.8 kg, 5.75 volumes) was charged to the reactor followed by N-hydroxyphthalimide (26.4 kg, 1.07 equivalents). The contents were warmed to 20±5° C. then agitated at this temperature for at least 5 hours, until the triflate intermediate was not detectable by TLC. The reaction mixture was split into two equal portions. Each toluene solution was quenched with USP purified water (66 kg, 6.7 volumes). The toluene solution was then washed twice with USP purified water (66 kg, 6.7 volumes).

The toluene solutions were recombined in a 100-gallon reactor. The organic solution was treated with 28% ammonium hydroxide solution (41.5 kg, 7.8 equivalents). The contents were heated to 35±5° C. then agitated for not less than ("NLT") 12 hours. Upon reaction completion, the lower, aqueous phase was removed. The toluene solution was dried via azeotropic distillation of toluene. The toluene solution was then concentrated to minimum stir volume. The concentrated solution was filtered to remove by-product solids. The cake was washed with toluene and the filtrates were combined. Assay of the toluene solution indicated 8.6 kg (36.7% yield) of PD-0337792 (IPGA) was present.

Step 2 (Preparation of PD-0315209): A clean, dry 100-gallon reactor was purged with nitrogen then charged with lithium amide (LiNH2, 8.8 kg, 3.4 equivalents) followed by tetrahydrofuran (THF, 56.8 kg, 3.2 volumes). The mixture was cooled to 10±10° C. then additional THF (15.1 kg, 0.85 volumes) was charged to the reactor, followed by a solution of 2,3,4-trifluorobenzoic acid (TFBA, 20.0 kg, 1.0 equivalent) in THF (26.4 kg, 1.15 volumes). The reaction mixture was heated to NMT ("not more than") 50° C. A solution of 2-flouro-4-iodoaniline (FIA, 27.5 kg, 1.02 equivalents) in THF (17.8 kg, 1 volumes) was added portion wise to the reactor, maintaining the batch temperature at NMT 50° C. and stirring for 1 hour between additions. After completing the additions, the reaction mixture stirred for an additional 3 hours at 50±10° C. Upon reaction completion, the mixture was cooled to NMT 10° C. then quenched with USP purified water (120.3 kg, 6 volumes). The reaction mixture was distilled to approximately 30 gallons after which methyl t-butyl ether (MTBE, 118.6 kg, 8 volumes) was added. The MTBE solution was then quenched with 2M hydrochloric acid solution (89.5 kg) to a pH=7. The aqueous phase was then removed. The MTBE solution was filtered through celite then washed twice with 5% brine solution (104.1 kg, 5.2 volumes) followed by 1M hydrochloric acid solution (77.4 kg). The MTBE solution was solvent swapped with toluene followed by volume adjustment to approximately 50 gallons. This mixture was heated to 75±5° C. for 1 hour then cooled to 20±5° C. and stirred for 1 hour. The product was filtered, washed with toluene (68.1 kg, ~4 volumes), then dried under vacuum at 40° C. to obtain 25.2 kg of PD-0315209 (56.4% yield).

Step 3 (Preparation of crude PD-0325901): A clean, dry 100-gallon reactor was purged with nitrogen then charged with PD-0315209 (18.0 kg, 1 equivalent) and THF (113.0 kg, 7 volumes). The mixture was cooled to 5±5° C. N,N-diisopropylethylamine (15.1 kg, 2.55 equivalents) was charged maintaining the temperature NMT 25° C. The mixture was cooled to 5±5° C. then stirred for 10 minutes. PD-0337792 solution in toluene (121.7 kg total, 1.3 equivalents) was charged to the reactor at 5±5° C., followed by 50% T3P in ethyl acetate (42.0 kg, 1.45 equivalents). The reaction mixture stirred at 10±5° C. for NLT 3 hours. An additional charge of N,N-diisopropylethylamine (1.9 kg, 0.3 equivalents) and 50% T3P in ethyl acetate (4.1 kg, 0.15 equivalents) were made to advance the coupling to completion. The reaction was reverse quenched into a 5% sodium hydroxide solution (50 kg), followed by washing with 5% brine (55.4 kg). The organic solution was concentrated then solvent swapped with toluene. Acetonitrile (43.0 kg, 2.4 volumes) was added to the reactor followed by 2M hydrochloric acid (117.6 kg, 5.1 equivalents). The mixture stirred at 25±5° C. until reaction completion after 16 hours. The bottom aqueous was removed then the reaction mixture was washed with 5% brine (75.2 kg). The organic phase was concentrated then solvent swapped with toluene to an appropriate volume. The mixture was then heated to 75±5° C. for 30 minutes then slowly cooled to 20° C. The solids were filtered then washed with toluene (31.1 kg, 1.7 volumes)

The crude solids were charged back to the 100-gallon reactor, followed by 5% ethanol in toluene (170.0 kg). The mixture was heated to 75±5° C. for 60 minutes to achieve a solution then slowly cooled to 20° C. The solids were filtered then washed twice with toluene (31 kg, 1.7 volumes). The wet cake was dried under vacuum at 45° C. to obtain 8.2 kg of crude PD-0325901 (37.1% yield).

Step 4 (Preparation of Essentially Pure Form IV Mirdametinib): A clean, dry 100-gallon reactor was purged with nitrogen then charged with USP Purified Water (164.1 kg, 20 volumes) followed by ethanol (200 proof, 20.8 kg, 3.25 volumes). The solution was heated to 35±5° C. In a separate vessel, crude PD-0325901 (8.1 kg, 1 equivalent) was dissolved in ethanol (200 proof, 40.5 kg, 6.3 volumes). A portion of this solution (14.4 kg) was added to the 100-gallon reactor over 60 minutes. PD-0325901 Form IV seeds as prepared in Example 1 (82.6 g, 1% wt) was added to the reactor to facilitate precipitation. The remainder of the crude PD-0325901/ethanol solution (34.3 kg) was added to the reactor over 90 minutes as the mixture stirred at 35±5° C. The reactor contents continued to stir at 35±5° C. for 5.5 hours then were slowly cooled to 20° C. The solids were then filtered, washed with USP purified water (16.5 kg, 2 volumes), then dried under vacuum at 45° C. for 16 hours. The dried solids were screened through a 10-mesh sieve to obtain 5.7 kg PD-0325901 Form IV (70.4% yield).

An XRPD pattern for essentially pure Form IV used herein is shown in FIG. 1A. TGA and DSC analysis of essentially pure Form IV used herein are shown in FIG. 1B.

Example 4: 0.5 mg and 1.0 mg Dispersible Tablet Formulations

Examples of dispersible tablet formulations are shown in Table 1.

TABLE 1

| | | Formulation Composition | | | |
|---|---|---|---|---|---|
| | | 0.5 mg | | 1.0 mg | |
| Ingredient | Function | % (w/w) | mg/ tab | % (w/w) | mg/ tab |
| Mirdametinib [a] | Active Ingredient | 0.75 | 0.50 | 0.75 | 1.00 |
| Microcrystalline Cellulose [b] | Diluent | 90.52 | 60.60 | 90.52 | 121.20 |
| Croscarmellose sodium | Disintegrant | 4.85 | 3.25 | 4.85 | 6.50 |
| Grape flavor | Flavor | 1.94 | 1.30 | 1.94 | 2.60 |
| Sucralose | Sweetener | 0.97 | 0.65 | 0.97 | 1.30 |
| Magnesium Stearate | Lubricant | 0.97 | 0.65 | 0.97 | 1.30 |
| Total | | 100.00 | 66.95 | 100.00 | 133.90 |

[a] = Based on theoretical potency of 1.000. Quantity may be adjusted based on the actual potency.
[b] = Quantity of microcrystalline cellulose can be adjusted for slight potency changes of mirdametinib

Example 5: A Manufacturing Process for Mirdametinib Dispersible Tablets

A non-limiting example of an exemplary process for producing mirdametinib dispersible tablets is described herein.

Microcrystalline cellulose (approximately 30% w/w of microcrystalline cellulose in final composition) is blended in a vessel. Mirdametinib, croscarmellose, and microcrystalline cellulose (approximately 50% w/w of microcrystalline cellulose in final composition) are added to the vessel and blended. The remaining microcrystalline cellulose is added to the vessel and blended. Intragranular magnesium stearate is added for lubrication, and the blend is roller compacted into dry granules. Grape flavor and sucralose are blended into the granules, and extragranular magnesium stearate is added for lubrication. The blend is compressed, and checked for in-process control based on appearance, weight, thickness, hardness, friability, and disintegration. The tablets are dedusted and checked for metal impurities, then bulk packaged.

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

In addition to the various embodiments described herein, the present disclosure includes the following embodiments numbered E1 through E141. This list of embodiments is presented as an exemplary list and the application is not limited to these embodiments.

E1. A pharmaceutical composition comprising an amount of N—((R)-2,3-dihydroxypropoxy)-3,4-difluoro-2-(2-fluoro-4-iodo-phenylamino)-benzamide of Formula (I)

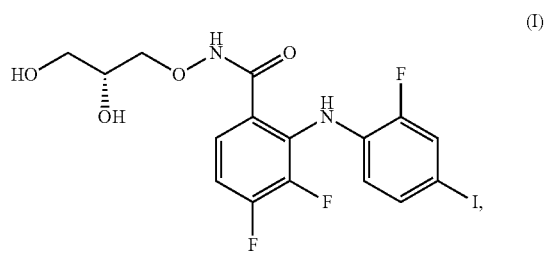 [SMILES: O=C(NOC[C@H](O)CO)c1ccc(F)c(F)c1Nc1ccc(I)cc1F]

wherein the pharmaceutical composition is dispersible in a potable liquid or orodispersible in a subject's saliva.

E2. The pharmaceutical composition of E1, wherein the N—((R)-2,3-dihydroxypropoxy)-3,4-difluoro-2-(2-fluoro-4-iodo-phenylamino)-benzamide is crystalline.

E3. The pharmaceutical composition of E2, wherein the crystalline form of N—((R)-2,3-dihydroxypropoxy)-3,4-difluoro-2-(2-fluoro-4-iodo-phenylamino)-benzamide is selected from the group consisting of:
  a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 7.3±0.2, and 14.6±0.2 degrees two theta;
  a crystalline form of N—((R)-2,3-dihydroxypropoxy)-3,4-difluoro-2-(2-fluoro-4-iodo-phenylamino)-benzamide characterized by an XRPD pattern having peaks at one or more of 10.6±0.2, 13.7±0.2, 19.0±0.2, and 23.7±0.2 degrees two theta; and
  a crystalline form of N—((R)-2,3-dihydroxypropoxy)-3,4-difluoro-2-(2-fluoro-4-iodo-phenylamino)-benzamide characterized by an XRPD pattern having peaks at one or more of 5.5±0.2 and 19.6±0.2 degrees two theta.

E4. The pharmaceutical composition of E2 or E3, wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 7.3±0.2, and 14.6±0.2 degrees two theta.

E5. The pharmaceutical composition of any one of E2-E4, wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 7.3±0.2, 14.6±0.2, and 25.0±0.2 degrees two theta.

E6. The pharmaceutical composition of any one of E2-E5, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 1A.

E7. The pharmaceutical composition of any one of E2-E6, wherein the crystalline form of N—((R)-2,3-dihydroxypropoxy)-3,4-difluoro-2-(2-fluoro-4-iodo-phenylamino)-benzamide is characterized by one or both of:
  a) a TGA profile substantially as shown in FIG. 1B; and/or
  b) a DSC profile substantially as shown in FIG. 1B.

E8. The pharmaceutical composition of any one of E2-E7, wherein the crystalline form of N—((R)-2,3-dihydroxypropoxy)-3,4-difluoro-2-(2-fluoro-4-iodo-phenylamino)-benzamide is characterized by a DSC profile which does not include an endotherm with an onset at about 117° C.

E9. The pharmaceutical composition of any one of E2-E8, wherein the crystalline form of N—((R)-2,3-dihydroxypropoxy)-3,4-difluoro-2-(2-fluoro-4-iodo-phenylamino)-benzamide does not contain any amount of Form I or Form II detectable by XRPD and/or DSC.

E10. The pharmaceutical composition of any one of E2-E9, wherein the crystalline form of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 3 months at standard warehouse conditions (15° C.-25° C. and ≤65% relative humidity).

E11. The pharmaceutical composition of any one of E2-E10, wherein the crystalline form of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 6 months at standard warehouse conditions (15° C.-25° C. and ≤65% relative humidity).

E12. The pharmaceutical composition of any one of E2-E11, wherein the crystalline form of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 1 year at standard warehouse conditions (15° C.-25° C. and ≤65% relative humidity).

E13. The pharmaceutical composition of any one of E2-E12, wherein the crystalline form of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for 68 months at standard warehouse conditions (15° C.-25° C. and ≤65% relative humidity).

E14. The pharmaceutical composition of any one of E2-E13, wherein the crystalline form of N—((R)-2,3-dihydroxypropoxy)-3,4-difluoro-2-(2-fluoro-4-iodo-phenylamino)-benzamide exhibits an XRPD pattern and/or DSC profile which is substantially unchanged after storage for ≥140 months at standard warehouse conditions (15° C.-25° C. and ≤65% relative humidity).

E15. The pharmaceutical composition of any one of E2-E14, wherein the DSC pattern is generated using a TA Instruments Q100 or Q2000 differential scanning calorimeter at a rate of temperature increase of about 15° C./min.

E16. The pharmaceutical composition of any one of E2-E15, wherein the crystalline form is anhydrous.

E17. The pharmaceutical composition of any one of E2-E16, wherein the crystalline form is Form IV.

E18. The pharmaceutical composition of E2 or E3, wherein the crystalline form of N—((R)-2,3-dihydroxypropoxy)-3,4-difluoro-2-(2-fluoro-4-iodo-phenylamino)-benzamide is characterized by an XRPD pattern having peaks at one or more of 10.6±0.2, 13.7±0.2, 19.0±0.2, and 23.7±0.2 degrees two theta.

E19. The pharmaceutical composition of E2, E3, or E18, wherein the crystalline form of N—((R)-2,3-dihydroxypropoxy)-3,4-difluoro-2-(2-fluoro-4-iodo-phenylamino)-benzamide is characterized by an XRPD pattern having peaks at one or more of 10.6±0.2, 13.7±0.2, 14.6±0.2, 17.3±0.2, 18.0±0.2, 18.2±0.2, 19.0±0.2, 19.3±0.2, 20.1±0.2, 21.0±0.2, 21.9±0.2, 22.4±0.2, 23.7±0.2, 24.0±0.2, 24.9±0.2, 26.3±0.2, 27.6±0.2, 28.0±0.2, 30.1±0.2, 32.1±0.2, 32.3±0.2, 32.9±0.2, 35.8±0.2, and 37.7±0.2 degrees two theta.

E20. The pharmaceutical composition of E2, E3, E18, or E19, wherein the crystalline form is characterized by a DSC profile with an endotherm with onset at about 117° C.

E21. The pharmaceutical composition of any one of E2, E3, and E18-E20, wherein the crystalline form is Form I.

E22. The pharmaceutical composition of E2 or E3, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2 and/or 19.6±0.2 degrees two theta.

E23. The pharmaceutical composition of E2, E3, or E22, wherein the crystalline form of N—((R)-2,3-dihydroxypropoxy)-3,4-difluoro-2-(2-fluoro-4-iodo-phenylamino)-benzamide is characterized by an XRPD pattern having peaks at one or more of 5.5±0.2, 10.7±0.2, 16.5±0.2, 19.6±0.2, 22.0±0.2, 22.5±0.2, 23.6±0.2, 24.1±0.2, 25.0±0.2, 26.2±0.2, 27.6±0.2, 29.1±0.2, 30.5±0.2, 31.7±0.2, 33.3±0.2, and 39.0±0.2 degrees two theta.

E24. The pharmaceutical composition of E2, E3, E22, or E23, wherein the crystalline form of N—((R)-2,3-dihydroxypropoxy)-3,4-difluoro-2-(2-fluoro-4-iodo-phenylamino)-benzamide is characterized by a DSC profile with an endotherm with onset at about 87° C.

E25. The pharmaceutical composition of any one of E2, E3, and E22-E24, wherein the crystalline form is Form II.

E26. The pharmaceutical composition of any one of E1-E25, wherein the pharmaceutical composition further comprises one or more pharmaceutically acceptable carriers.

E27. The pharmaceutical composition of any one of E1-E26, wherein the pharmaceutical composition is for oral administration.

E28. The pharmaceutical composition of any one of E1-E27, wherein the pharmaceutical composition is orodispersible.

E29. The pharmaceutical composition of any one of E1-E28, wherein the pharmaceutical composition is a tablet, a powder, granules, minitablets, or pellets.

E30. The pharmaceutical composition of E29, wherein the pharmaceutical composition is a powder.

E31. The pharmaceutical composition of E30, wherein the powder is a dispersible powder.

E32. The pharmaceutical composition of E30 or E31, wherein a capsule or sachet comprises the powder or dispersible powder.

E33. The pharmaceutical composition of E29, wherein the pharmaceutical composition is in the form of granules.

E34. The pharmaceutical composition of E33, wherein the granules are dispersible granules.

E35. The pharmaceutical composition of E33 or E34, wherein a capsule or sachet comprises the granules or dispersible granules.

E36. The pharmaceutical composition of E29, wherein the pharmaceutical composition is in the form of minitablets.

E37. The pharmaceutical composition of E36, wherein the minitablets are dispersible minitablets.

E38. The pharmaceutical composition of E36 or E37, wherein a capsule or sachet comprises the minitablets or dispersible minitablets.

E39. The pharmaceutical composition of E29, wherein the pharmaceutical composition is in the form of pellets.

E40. The pharmaceutical composition of E39, wherein the pellets are dispersible pellets.

E41. The pharmaceutical composition of E39 or E40, wherein a capsule or sachet comprises the minitablets or dispersible minitablets.

E42. The pharmaceutical composition of E29, wherein pharmaceutical composition is a tablet.

E43. The pharmaceutical composition of E42, wherein the pharmaceutical composition is a dispersible tablet.

E44. The pharmaceutical composition of any one of E1-E43, comprising:
about 0.1 mg to about 20 mg of N—((R)-2,3-dihydroxypropoxy)-3,4-difluoro-2-(2-fluoro-4-iodo-phenylamino)-benzamide;
and wherein each component of the pharmaceutical composition is as follows:
a. about 0.1 wt/wt % to about 7 wt/wt % of N—((R)-2,3-dihydroxypropoxy)-3,4-difluoro-2-(2-fluoro-4-iodo-phenylamino)-benzamide;
b. about 50 wt/wt % to about 98 wt/wt % of one or more diluents;
c. about 1 wt/wt % to about 10 wt/wt % of one or more disintegrants;
d. 0 wt/wt % to about 5 wt/wt % of one or more flavoring agents;
e. 0 wt/wt % to about 5 wt/wt % of one or more sweeteners; and
f. about 0 wt/wt % to about 5 wt/wt % of one or more lubricants.

E45. The pharmaceutical composition of any one of E1-E43, comprising: about 0.1 mg to about 20 mg of N—((R)-2,3-dihydroxypropoxy)-3,4-difluoro-2-(2-fluoro-4-iodo-phenylamino)-benzamide;
and wherein each component of the pharmaceutical composition is as follows:
a. about 0.5 wt/wt % to about 1.2 wt/wt % of N—((R)-2,3-dihydroxypropoxy)-3,4-difluoro-2-(2-fluoro-4-iodo-phenylamino)-benzamide;
b. about 85 wt/wt % to about 95 wt/wt % of one or more diluents;
c. about 3.5 wt/wt % to about 6 wt/wt % of one or more disintegrants;
d. 0 wt/wt % to about 2.5 wt/wt % of one or more flavoring agents;
e. 0 wt/wt % to about 2 wt/wt % of one or more sweeteners; and
f. about 0.5 wt/wt % to about 2 wt/wt % of one or more lubricants.

E46. The pharmaceutical composition of E44 or E45, wherein the pharmaceutical composition comprises about 0.5 mg of N—((R)-2,3-dihydroxypropoxy)-3,4-difluoro-2-(2-fluoro-4-iodo-phenylamino)-benzamide.

E47. The pharmaceutical composition of E44 or E45, wherein the pharmaceutical composition comprises about 1 mg of N—((R)-2,3-dihydroxypropoxy)-3,4-difluoro-2-(2-fluoro-4-iodo-phenylamino)-benzamide.

E48. The pharmaceutical composition of E44 or E45, wherein the pharmaceutical composition comprises about 2 mg of N—((R)-2,3-dihydroxypropoxy)-3,4-difluoro-2-(2-fluoro-4-iodo-phenylamino)-benzamide.

E49. The pharmaceutical composition of E44 or E45, wherein the pharmaceutical composition comprises about 3 mg of N—((R)-2,3-dihydroxypropoxy)-3,4-difluoro-2-(2-fluoro-4-iodo-phenylamino)-benzamide.

E50. The pharmaceutical composition of E44 or E45, wherein the pharmaceutical composition comprises about 4 mg of N—((R)-2,3-dihydroxypropoxy)-3,4-difluoro-2-(2-fluoro-4-iodo-phenylamino)-benzamide.

E51. The pharmaceutical composition of any one of E44-E50, wherein at least one of the diluents is selected from the group consisting of microcrystalline cellulose, lactose, mannitol, starch, sorbitol, xylitol, sucrose, pregelatinized starch, calcium sulfate, calcium carbonate, and dibasic calcium phosphate.

E52. The pharmaceutical composition of E51, wherein at least one of the diluents is microcrystalline cellulose.

E53. The pharmaceutical composition of any one of E44-E52, wherein at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid.

E54. The pharmaceutical composition of E53, wherein at least one of the disintegrants is croscarmellose sodium.

E55. The pharmaceutical composition of any one of E44-E54, wherein at least one of the flavoring agents is selected from the group consisting of natural or synthetic flavors including but not limited to, grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring.

E56. The pharmaceutical composition of E55, wherein at least one of the flavoring agents is grape flavoring.

E57. The pharmaceutical composition of any one of E44-E56, wherein at least one of the sweeteners is selected from the group consisting of sucralose, acesulfame, saccharin, sucrose, xylitol, mannitol, sorbitol, glucose, fructose, and aspartame.

E58. The pharmaceutical composition of E57, wherein at least one of the sweeteners is sucralose.

E59. The pharmaceutical composition of any one of E44-E58, wherein at least one of the lubricants is selected from the group consisting of magnesium stearate, sodium stearyl fumarate, glycerol dibehenate, stearic acid, calcium stearate, zinc stearate, beeswax, colloidal silicon dioxide, hydrogenated vegetable oil, and talc.

E60. The pharmaceutical composition of E59, wherein at least one of the lubricants is magnesium stearate.

E61. The pharmaceutical composition of any one of E1-E60, wherein the potable liquid is water milk or a juice.

E62. The pharmaceutical composition of any one of E1-E60, wherein the pharmaceutical composition is dispersible in a subject's saliva.

E63. A method of treating a tumor, a cancer, or a Rasopathy disorder comprising administering to a subject in need of such treatment the pharmaceutical composition of any one of E1-E62.

E64. The method of E63, wherein the tumor is a neurofibroma.

E65. The method of E64, wherein the tumor is a neurofibroma associated with Neurofibromatosis Type 1.

E66. The method of any one of E63-E65, wherein the tumor is selected from the group consisting of cutaneous neurofibroma, plexiform neurofibroma, optic pathway glioma, low grade glioma, high grade glioma, or malignant peripheral nerve sheath tumor.

E67. The method of E66, wherein the tumor is plexiform neurofibroma.

E68. The method of E67, wherein the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

E69. The method of E63, wherein the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum.

E70. The method of E69, wherein the leukemia is selected from the group consisting of acute lymphocytic leukemia, acute myelogenous leukemia, chronic lymphocytic leukemia, and chronic myelogenous leukemia.

E71. The method of E69, wherein the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia.

E72. The method of E69, wherein the lung cancer is selected from the group consisting of lung adenocarcinoma, squamous non-small cell lung cancer, non-squamous non-small cell lung cancer, and small cell lung cancer.

E73. The method of any one of E63-E72, wherein the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

E74. The method of any one of E63-E73, wherein an individual dose of the N—((R)-2,3-dihydroxypropoxy)-3,4-difluoro-2-(2-fluoro-4-iodo-phenylamino)-benzamide is administered as more than one tablet, more than one dose of dispersible powder, more than one dose of dispersible granules, more than one dose of minitablets, more than one dose of pellets, or a combination thereof.

E75. The method of any one of E63-E74, wherein the N—((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N—((R)-2,3-dihydroxypropoxy)-3,4-difluoro-2-(2-fluoro-4-iodo-phenylamino)-benzamide is administered.

E76. The method of any one of E63-E74, wherein the N—((R)-2,3-dihydroxypropoxy)-3,4-difluoro-2-(2-fluoro-4-iodo-phenylamino)-benzamide is administered on a 28-day dosing cycle comprising (a) 21 consecutive days in which the total daily dose is administered; followed by (b) 7 consecutive days in which no N—((R)-2,3-dihydroxypropoxy)-3,4-difluoro-2-(2-fluoro-4-iodo-phenylamino)-benzamide is administered.

E77. The method of any one of E63-E74, wherein the N—((R)-2,3-dihydroxypropoxy)-3,4-difluoro-2-(2-fluoro-4-iodo-phenylamino)-benzamide is administered on a 28-day dosing cycle comprising (a) three 7-day periods each comprising (i) 5 days in which the total daily dose is administered and (ii) 2 days in which no N—((R)-2,3-dihydroxypropoxy)-3,4-difluoro-2-(2-fluoro-4-iodo-phenylamino)-benzamide; and (b) 7 days in which no N—((R)-2,3-dihydroxypropoxy)-3,4-difluoro-2-(2-fluoro-4-iodo-phenylamino)-benzamide is administered.

E78. The method of any one of E63-E74, wherein the N—((R)-2,3-dihydroxypropoxy)-3,4-difluoro-2-(2-fluoro-4-iodo-phenylamino)-benzamide is administered on a 28-day dosing cycle comprising (a) three 7-day periods each comprising (i) 5 consecutive days in which the total daily dose is administered and (ii) 2 consecutive days in which no N—((R)-2,3-dihydroxypropoxy)-3,4-difluoro-2-(2-fluoro-4-iodo-phenylamino)-benzamide; followed by (b) 7 consecutive days in which no N—((R)-2,3-dihydroxypropoxy)-3,4-difluoro-2-(2-fluoro-4-iodo-phenylamino)-benzamide is administered.

E79. The method of any one of E63-E74, wherein the N—((R)-2,3-dihydroxypropoxy)-3,4-difluoro-2-(2-fluoro-4-iodo-phenylamino)-benzamide is administered on a 28-day dosing cycle comprising 28 days in which the total daily dose is administered.

E80. The method of any one of E78-E79, wherein the 28-day dosing cycle is repeated up to a total of 24 consecutive 28-day dosing cycles.

E81. The method of any one of E63-E80, wherein the subject experiences dysphagia.

E82. The method of E81, wherein the subject experiences dysphagia caused by one or more of: disease of the nervous system, muscle weakening, developmental disability, stroke, injury, anatomical defect, cancer, treatment for cancer, allergic reaction, dementia, memory loss, or cognitive decline.

E83. The method of any one of E63-E80, wherein the subject is a pediatric subject.

E84. The method of any one of claims E63-E83, wherein the total daily dose of N—((R)-2,3-dihydroxypropoxy)-3,4-difluoro-2-(2-fluoro-4-iodo-phenylamino)-benzamide is administered two times daily.

E85. The method of E84, wherein the total daily dose of the N—((R)-2,3-dihydroxypropoxy)-3,4-difluoro-2-(2-fluoro-4-iodo-phenylamino)-benzamide is administered two times daily at a dose of about 0.1 mg to about 10 mg each.

E86. The method of E85, wherein the total daily dose of the N—((R)-2,3-dihydroxypropoxy)-3,4-difluoro-2-(2-fluoro-4-iodo-phenylamino)-benzamide is administered two times daily at a dose of about 0.25 mg each.

E87. The method of E85, wherein the total daily dose of the N—((R)-2,3-dihydroxypropoxy)-3,4-difluoro-2-(2-fluoro-4-iodo-phenylamino)-benzamide is administered two times daily at a dose of about 0.5 mg each.

E88. The method of E85, wherein the total daily dose of the N—((R)-2,3-dihydroxypropoxy)-3,4-difluoro-2-(2-fluoro-4-iodo-phenylamino)-benzamide is administered two times daily at a dose of about 1 mg each.

E89. The method of E85, wherein the total daily dose of the N—((R)-2,3-dihydroxypropoxy)-3,4-difluoro-2-(2-fluoro-4-iodo-phenylamino)-benzamide is administered two times daily at a dose of about 2 mg each.

E90. The method of E85, wherein the total daily dose of the N—((R)-2,3-dihydroxypropoxy)-3,4-difluoro-2-(2-fluoro-4-iodo-phenylamino)-benzamide is administered two times daily at a dose of about 4 mg each.

E91. The method of E85, wherein the total daily dose of the N—((R)-2,3-dihydroxypropoxy)-3,4-difluoro-2-(2-fluoro-4-iodo-phenylamino)-benzamide is administered two times daily at a dose of about 5 mg each.

E92. The method of E85, wherein the total daily dose of the N—((R)-2,3-dihydroxypropoxy)-3,4-difluoro-2-(2-fluoro-4-iodo-phenylamino)-benzamide is administered two times daily at a dose of about 10 mg each.

E93. The method of any one of E63-E83, wherein the total daily dose of the N—((R)-2,3-dihydroxypropoxy)-3,4-difluoro-2-(2-fluoro-4-iodo-phenylamino)-benzamide is administered once daily.

E94. The method of E93, wherein the total daily dose of the N—((R)-2,3-dihydroxypropoxy)-3,4-difluoro-2-(2-fluoro-4-iodo-phenylamino)-benzamide is administered once daily at a dose of about 0.1 mg to about 20 mg.

E95. The method of E94, wherein the total daily dose of the N—((R)-2,3-dihydroxypropoxy)-3,4-difluoro-2-(2- fluoro-4-iodo-phenylamino)-benzamide is administered once daily at a dose of about 0.5 mg.

E96. The method of E94, wherein the total daily dose of the N—((R)-2,3-dihydroxypropoxy)-3,4-difluoro-2-(2-fluoro-4-iodo-phenylamino)-benzamide is administered once daily at a dose of about 1 mg.

E97. The method of E94, wherein the total daily dose of the N—((R)-2,3-dihydroxypropoxy)-3,4-difluoro-2-(2-fluoro-4-iodo-phenylamino)-benzamide is administered once daily at a dose of about 2 mg.

E98. The method of E94, wherein the total daily dose of the N—((R)-2,3-dihydroxypropoxy)-3,4-difluoro-2-(2-fluoro-4-iodo-phenylamino)-benzamide is administered once daily at a dose of about 4 mg.

E99. The method of E94, wherein the total daily dose of the N—((R)-2,3-dihydroxypropoxy)-3,4-difluoro-2-(2-fluoro-4-iodo-phenylamino)-benzamide is administered once daily at a dose of about 8 mg.

E100. The method of E94, wherein the total daily dose of the N—((R)-2,3-dihydroxypropoxy)-3,4-difluoro-2-(2-fluoro-4-iodo-phenylamino)-benzamide is administered once daily at a dose of about 10 mg.

E101. The method of E94, wherein the total daily dose of the N—((R)-2,3-dihydroxypropoxy)-3,4-difluoro-2-(2-fluoro-4-iodo-phenylamino)-benzamide is administered once daily at a dose of about 20 mg.

E102. The method of any one of E63-E101, wherein the N—((R)-2,3-dihydroxypropoxy)-3,4-difluoro-2-(2-fluoro-4-iodo-phenylamino)-benzamide is administered in a total daily dose that does not exceed 20 mg.

E103. The method of any one of claims E63-E101, wherein the N—((R)-2,3-dihydroxypropoxy)-3,4-difluoro-2-(2-fluoro-4-iodo-phenylamino)-benzamide is administered in a total daily dose that does not exceed 10 mg.

E104. The method of any one of claims E63-E101, wherein the N—((R)-2,3-dihydroxypropoxy)-3,4-difluoro-2-(2-fluoro-4-iodo-phenylamino)-benzamide is administered in a total daily dose that does not exceed 8 mg.

E105. The method of any one of E63-E101, wherein the N—((R)-2,3-dihydroxypropoxy)-3,4-difluoro-2-(2-fluoro-4-iodo-phenylamino)-benzamide is administered in a total daily dose that does not exceed 6 mg.

E106. The method of any one of E63-E101, wherein the N—((R)-2,3-dihydroxypropoxy)-3,4-difluoro-2-(2-fluoro-4-iodo-phenylamino)-benzamide is administered in a total daily dose that does not exceed 4 mg.

E107. The method of any one of E63-E101, wherein the N—((R)-2,3-dihydroxypropoxy)-3,4-difluoro-2-(2-fluoro-4-iodo-phenylamino)-benzamide is administered in a total daily dose that does not exceed 2 mg.

E108. The method of any one of E63-E101, wherein the N—((R)-2,3-dihydroxypropoxy)-3,4-difluoro-2-(2-fluoro-4-iodo-phenylamino)-benzamide is administered in a total daily dose that does not exceed 1 mg.

E109. Use of the pharmaceutical composition of any one of E1-E62 for the manufacture of a medicament for treating a tumor, a cancer, or a Rasopathy disorder.

E110. The use of E109, wherein the tumor is a neurofibroma.

E111. The use of E110, wherein the tumor is a neurofibroma associated with Neurofibromatosis Type 1.

E112. The use of any one of E109-E111, wherein the tumor is selected from the group consisting of cutaneous neurofibroma, plexiform neurofibroma, optic pathway glioma, low grade glioma, high grade glioma, or malignant peripheral nerve sheath tumor.

E113. The use of E112, wherein the tumor is plexiform neurofibroma.

E114. The use of E109, wherein the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

E115. The use of E109, wherein the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum.

E116. The use of E115, wherein the leukemia is selected from the group consisting of acute lymphocytic leukemia, acute myelogenous leukemia, chronic lymphocytic leukemia, and chronic myelogenous leukemia.

E117. The use of E115, wherein the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia.

E118. The use of E115, wherein the lung cancer is selected from the group consisting of lung adenocarcinoma, squamous non-small cell lung cancer, non-squamous non-small cell lung cancer, and small cell lung cancer.

E119. The use of any one of E109-E118, wherein the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

E120. The use of any one of E109-E119, wherein an individual dose of the N—((R)-2,3-dihydroxypropoxy)-3,4-difluoro-2-(2-fluoro-4-iodo-phenylamino)-benzamide is administered as more than one tablet, more than one dose of dispersible powder, more than one dose of dispersible granules, more than one dose of minitablets, more than one dose of pellets, or a combination thereof.

E121. The use of any one of E109-E119, wherein the N—((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N—((R)-2,3-dihydroxypropoxy)-3,4-difluoro-2-(2-fluoro-4-iodo-phenylamino)-benzamide is administered.

E122. The use of any one of E109-E119, wherein the N—((R)-2,3-dihydroxypropoxy)-3,4-difluoro-2-(2-fluoro-4-iodo-phenylamino)-benzamide is administered on a 28-day dosing cycle comprising (a) 21 consecutive days in which the total daily dose is administered; followed by (b) 7 consecutive days in which no N—((R)-2,3-dihydroxypropoxy)-3,4-difluoro-2-(2-fluoro-4-iodo-phenylamino)-benzamide is administered.

E123. The use of any one of E109-E119, wherein the N—((R)-2,3-dihydroxypropoxy)-3,4-difluoro-2-(2-fluoro-4-iodo-phenylamino)-benzamide is administered on a 28-day dosing cycle comprising (a) three 7-day periods each comprising (i) 5 days in which the total daily dose is administered and (ii) 2 days in which no N—((R)-2,3-dihydroxypropoxy)-3,4-difluoro-2-(2-fluoro-4-iodo-phenylamino)-benzamide; and (b) 7 days in which no N—((R)-2,3-dihydroxypropoxy)-3,4-difluoro-2-(2-fluoro-4-iodo-phenylamino)-benzamide is administered.

E124. The use of any one of E109-E119, wherein the N—((R)-2,3-dihydroxypropoxy)-3,4-difluoro-2-(2-fluoro-4-iodo-phenylamino)-benzamide is administered on a 28-day dosing cycle comprising (a) three 7-day periods each comprising (i) 5 consecutive days in which the total daily dose is administered and (ii) 2 consecutive days in which no N—((R)-2,3-dihydroxypropoxy)-3,4-difluoro-2-(2-fluoro-4-iodo-phenylamino)-benzamide; followed by (b) 7 consecutive days in which no N—((R)-2,3-dihydroxypropoxy)-3,4-difluoro-2-(2-fluoro-4-iodo-phenylamino)-benzamide is administered.

E125. The use of any one of E109-E119, wherein the N—((R)-2,3-dihydroxypropoxy)-3,4-difluoro-2-(2-fluoro-4-iodo-phenylamino)-benzamide is administered on a 28-day dosing cycle comprising 28 days in which the total daily dose is administered.

E126. The use of any one of E124-E125, wherein the 28-day dosing cycle is repeated up to a total of 24 consecutive 28-day dosing cycles.

E127. The use of any one of E109-E126, wherein the subject experiences dysphagia.

E128. The use of E127, wherein the subject experiences dysphagia caused by one or more of: disease of the nervous system, muscle weakening, developmental disability, stroke, injury, anatomical defect, cancer, treatment for cancer, allergic reaction, dementia, memory loss, or cognitive decline.

E129. The use of any one of E109-E128, wherein the subject is a pediatric subject.

E130. The use of any one of E109-E129, wherein the total daily dose of N—((R)-2,3-dihydroxypropoxy)-3,4-difluoro-2-(2-fluoro-4-iodo-phenylamino)-benzamide is administered two times daily.

E131. The use of E130, wherein the total daily dose of the N—((R)-2,3-dihydroxypropoxy)-3,4-difluoro-2-(2-fluoro-4-iodo-phenylamino)-benzamide is administered two times daily at a dose of about 0.1 mg to about 10 mg each.

E132. The use of E131, wherein the total daily dose of the N—((R)-2,3-dihydroxypropoxy)-3,4-difluoro-2-(2-fluoro-4-iodo-phenylamino)-benzamide is administered two times daily at a dose of about 0.25 mg each.

E133. The use of E131, wherein the total daily dose of the N—((R)-2,3-dihydroxypropoxy)-3,4-difluoro-2-(2-fluoro-4-iodo-phenylamino)-benzamide is administered two times daily at a dose of about 0.5 mg each.

E134. The use of E131, wherein the total daily dose of the N—((R)-2,3-dihydroxypropoxy)-3,4-difluoro-2-(2-fluoro-4-iodo-phenylamino)-benzamide is administered two times daily at a dose of about 1 mg each.

E135. The use of E131, wherein the total daily dose of the N—((R)-2,3-dihydroxypropoxy)-3,4-difluoro-2-(2-fluoro-4-iodo-phenylamino)-benzamide is administered two times daily at a dose of about 2 mg each.

E136. The use of E131, wherein the total daily dose of the N—((R)-2,3-dihydroxypropoxy)-3,4-difluoro-2-(2-fluoro-4-iodo-phenylamino)-benzamide is administered two times daily at a dose of about 4 mg each.

E137. The use of E131, wherein the total daily dose of the N—((R)-2,3-dihydroxypropoxy)-3,4-difluoro-2-(2-fluoro-4-iodo-phenylamino)-benzamide is administered two times daily at a dose of about 5 mg each.

E138. The use of E131, wherein the total daily dose of the N—((R)-2,3-dihydroxypropoxy)-3,4-difluoro-2-(2-fluoro-4-iodo-phenylamino)-benzamide is administered two times daily at a dose of about 10 mg each.

E139. The use of any one of E109-E129, wherein the total daily dose of the N—((R)-2,3-difluoro-2-(2-fluoro-4-iodo-phenylamino)-benzamide is administered once daily.

E140. The use of E139, wherein the total daily dose of the N—((R)-2,3-dihydroxypropoxy)-3,4-difluoro-2-(2-fluoro-4-iodo-phenylamino)-benzamide is administered once daily at a dose of about 0.1 mg to about 20 mg.

E141. The use of E140, wherein the total daily dose of the N—((R)-2,3-dihydroxypropoxy)-3,4-difluoro-2-(2-fluoro-4-iodo-phenylamino)-benzamide is administered once daily at a dose of about 0.5 mg.

E142. The use of E140, wherein the total daily dose of the N—((R)-2,3-dihydroxypropoxy)-3,4-difluoro-2-(2-fluoro-4-iodo-phenylamino)-benzamide is administered once daily at a dose of about 1 mg.

E143. The use of E140, wherein the total daily dose of the N—((R)-2,3-dihydroxypropoxy)-3,4-difluoro-2-(2-fluoro-4-iodo-phenylamino)-benzamide is administered once daily at a dose of about 2 mg.

E144. The use of E140, wherein the total daily dose of the N—((R)-2,3-dihydroxypropoxy)-3,4-difluoro-2-(2-fluoro-4-iodo-phenylamino)-benzamide is administered once daily at a dose of about 4 mg.

E145. The use of E140, wherein the total daily dose of the N—((R)-2,3-dihydroxypropoxy)-3,4-difluoro-2-(2-fluoro-4-iodo-phenylamino)-benzamide is administered once daily at a dose of about 8 mg.

E146. The use of E140, wherein the total daily dose of the N—((R)-2,3-dihydroxypropoxy)-3,4-difluoro-2-(2-fluoro-4-iodo-phenylamino)-benzamide is administered once daily at a dose of about 10 mg.

E147. The use of E140, wherein the total daily dose of the N—((R)-2,3-dihydroxypropoxy)-3,4-difluoro-2-(2-fluoro-4-iodo-phenylamino)-benzamide is administered once daily at a dose of about 20 mg.

E148. The use of any one of E109-E147, wherein the N—((R)-2,3-dihydroxypropoxy)-3,4-difluoro-2-(2-fluoro-4-iodo-phenylamino)-benzamide is administered in a total daily dose that does not exceed 20 mg.

E149. The use of any one of E109-E148, wherein the N—((R)-2,3-dihydroxypropoxy)-3,4-difluoro-2-(2-fluoro-4-iodo-phenylamino)-benzamide is administered in a total daily dose that does not exceed 10 mg.

E150. The use of any one of E109-E148, wherein the N—((R)-2,3-dihydroxypropoxy)-3,4-difluoro-2-(2-fluoro-4-iodo-phenylamino)-benzamide is administered in a total daily dose that does not exceed 8 mg.

E151. The use of any one of E109-E148, wherein the N—((R)-2,3-dihydroxypropoxy)-3,4-difluoro-2-(2-fluoro-4-iodo-phenylamino)-benzamide is administered in a total daily dose that does not exceed 6 mg.

E152. The use of any one of E109-E148, wherein the N—((R)-2,3-dihydroxypropoxy)-3,4-difluoro-2-(2-fluoro-4-iodo-phenylamino)-benzamide is administered in a total daily dose that does not exceed 4 mg.

The use of any one of claims 109-148, wherein the N—((R)-2,3-dihydroxypropoxy)-3,4-difluoro-2-(2-fluoro-4-iodo-phenylamino)-benzamide is administered in a total daily dose that does not exceed 2 mg.

The use of any one of claims 109-148, wherein the N—((R)-2,3-dihydroxypropoxy)-3,4-difluoro-2-(2-fluoro- 4-iodo-phenylamino)-benzamide is administered in a total daily dose that does not exceed 1 mg.

What is claimed is:

1. A dispersible tablet comprising:
   a. about 0.5 mg of N—((R)-2,3-dihydroxypropoxy)-3,4-difluoro-2-(2-fluoro-4-iodo-phenylamino)-benzamide of Formula (I)

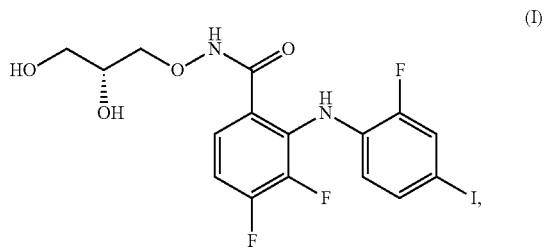 [SMILES: O=C(NOC[C@H](O)CO)c1ccc(F)c(F)c1Nc1ccc(I)cc1F]

wherein the N—((R)-2,3-dihydroxypropoxy)-3,4-difluoro-2-(2-fluoro-4-iodo-phenylamino)-benzamide constitutes about 0.1 wt/wt % to about 7 wt/wt % of the tablet;
   b. about 50 wt/wt % to about 98 wt/wt % of one or more diluents;
   c. about 1 wt/wt % to about 10 wt/wt % of one or more disintegrants;
   d. optionally one or more flavoring agents;
   e. optionally one or more sweeteners; and
   f. about 0 wt/wt % to about 5 wt/wt % of one or more lubricants.

2. The tablet of claim 1, wherein the N—((R)-2,3-dihydroxypropoxy)-3,4-difluoro-2-(2-fluoro-4-iodo-phenylamino)-benzamide is crystalline.

3. The tablet of claim 1, wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 7.3±0.2, and 14.6±0.2 degrees two theta.

4. The tablet of claim 1, wherein the tablet is orodispersible.

5. The tablet of claim 1, comprising:
   a. about 0.5 mg of N—((R)-2,3-dihydroxypropoxy)-3,4-difluoro-2-(2-fluoro-4-iodo-phenylamino)-benzamide, wherein the N—((R)-2,3-dihydroxypropoxy)-3,4-difluoro-2-(2-fluoro-4-iodo-phenylamino)-benzamide constitutes about 0.2 wt/wt % to about 1.5 wt/wt % of the tablet;
   b. about 85 wt/wt % to about 95 wt/wt % of one or more diluents;
   c. about 3.5 wt/wt % to about 6 wt/wt % of one or more disintegrants;
   d. grape flavor;
   e. sucralose; and
   f. about 0.5 wt/wt % to about 2 wt/wt % of one or more lubricants.

6. The tablet of claim 1, comprising:
   a. about 0.5 mg of N—((R)-2,3-dihydroxypropoxy)-3,4-difluoro-2-(2-fluoro-4-iodo-phenylamino)-benzamide;
   b. about 60.60 mg of microcrystalline cellulose;
   c. about 3.25 mg of croscarmellose sodium;
   d. grape flavor;
   e. 0.65 mg sucralose; and
   f. about 0.65 mg magnesium stearate.

7. A method of administering N—((R)-2,3-dihydroxypropoxy)-3,4-difluoro-2-(2-fluoro-4-iodo-phenylamino)-benzamide to a subject in need thereof comprising orally administering the tablet of claim 1.

8. The method of claim 7, wherein the subject is a pediatric patient.

9. A method of administering N—((R)-2,3-dihydroxypropoxy)-3,4-difluoro-2-(2-fluoro-4-iodo-phenylamino)-benzamide to a subject in need thereof comprising (i) combining a tablet of claim 1 with a potable liquid to form a solution, and (ii) orally administering the solution to the subject.

10. The method of claim 9, wherein the tablet disintegrates or dissolves within 10 minutes after being combined with a potable liquid.

11. A method of treating a human subject who has neurofibromatosis type 1 comprising (i) combining a tablet of claim 1 with a potable liquid to form a solution, and (ii) orally administering the solution to the subject.

12. The method of claim 11, wherein the subject has a neurofibroma associated with neurofibromatosis type 1.

13. The method of claim 11, wherein the potable liquid is water.

14. A dispersible tablet comprising:
   a. about 1 mg of N—((R)-2,3-dihydroxypropoxy)-3,4-difluoro-2-(2-fluoro-4-iodo-phenylamino)-benzamide of Formula (I)

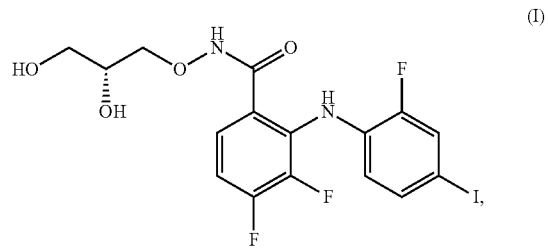 [SMILES: O=C(NOC[C@H](O)CO)c1ccc(F)c(F)c1Nc1ccc(I)cc1F]

wherein the N—((R)-2,3-dihydroxypropoxy)-3,4-difluoro-2-(2-fluoro-4-iodo-phenylamino)-benzamide constitutes about 0.1 wt/wt % to about 7 wt/wt % of the tablet;
   b. about 50 wt/wt % to about 98 wt/wt % of one or more diluents;
   c. about 1 wt/wt % to about 10 wt/wt % of one or more disintegrants;
   d. optionally one or more flavoring agents;
   e. optionally one or more sweeteners; and
   f. about 0 wt/wt % to about 5 wt/wt % of one or more lubricants.

15. The tablet of claim 14, wherein the N—((R)-2,3-dihydroxypropoxy)-3,4-difluoro-2-(2-fluoro-4-iodo-phenylamino)-benzamide is crystalline.

16. The tablet of claim 14, wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 7.3±0.2, and 14.6±0.2 degrees two theta.

17. The tablet of claim 14, wherein the tablet is orodispersible.

18. The tablet of claim 14, comprising:
   a. about 1 mg of N—((R)-2,3-dihydroxypropoxy)-3,4-difluoro-2-(2-fluoro-4-iodo-phenylamino)-benzamide, wherein the N—((R)-2,3-dihydroxypropoxy)-3,4-difluoro-2-(2-fluoro-4-iodo-phenylamino)-benzamide constitutes about 0.2 wt/wt % to about 1.5 wt/wt % of the tablet;

b. about 85 wt/wt % to about 95 wt/wt % of one or more diluents;
c. about 3.5 wt/wt % to about 6 wt/wt % of one or more disintegrants;
d. grape flavor;
e. sucralose; and
f. about 0.5 wt/wt % to about 2 wt/wt % of one or more lubricants.

19. The tablet of claim 14, comprising:
a. about 1 mg of N—((R)-2,3-dihydroxypropoxy)-3,4-difluoro-2-(2-fluoro-4-iodo-phenylamino)-benzamide;
b. about 121.20 mg of microcrystalline cellulose;
c. about 6.5 mg of croscarmellose sodium;
d. grape flavor;
e. 1.30 mg sucralose; and
f. about 1.30 mg magnesium stearate.

20. A method of administering N—((R)-2,3-dihydroxypropoxy)-3,4-difluoro-2-(2-fluoro-4-iodo-phenylamino)-benzamide to a subject in need thereof comprising orally administering the tablet of claim 14.

21. The method of claim 20, wherein the subject is a pediatric patient.

22. A method of administering N—((R)-2,3-dihydroxypropoxy)-3,4-difluoro-2-(2-fluoro-4-iodo-phenylamino)-benzamide to a subject in need thereof comprising (i) combining a tablet of claim 14 with a potable liquid to form a solution, and (ii) orally administering the solution to the subject.

23. The method of claim 22, wherein the tablet disintegrates or dissolves within 10 minutes after being combined with a potable liquid.

\* \* \* \* \*